United States Patent
Brown et al.

(10) Patent No.: US 9,986,809 B2
(45) Date of Patent: *Jun. 5, 2018

(54) AEROSOL HAIRSPRAY PRODUCT COMPRISING A SPRAYING DEVICE

(71) Applicant: The Procter & Gamble Company, Cincinnati, OH (US)

(72) Inventors: Jodi Lee Brown, Cincinnati, OH (US); Jose Antonio Carballada, Cincinnati, OH (US); Willy Benson, Harrison, OH (US); Matthew John Martin, California, KY (US); Kendrick Jon Hughes, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/315,950

(22) Filed: Jun. 26, 2014

(65) Prior Publication Data

US 2015/0004200 A1    Jan. 1, 2015

Related U.S. Application Data

(60) Provisional application No. 61/840,719, filed on Jun. 28, 2013.

(30) Foreign Application Priority Data

Jul. 30, 2013  (EP) ..................... 13178461

(51) Int. Cl.
| | |
|---|---|
| A45D 19/02 | (2006.01) |
| B05B 7/04 | (2006.01) |
| B65D 83/14 | (2006.01) |
| A61K 8/81 | (2006.01) |
| A61K 8/87 | (2006.01) |
| A61K 8/04 | (2006.01) |
| A61Q 5/06 | (2006.01) |
| B65D 83/44 | (2006.01) |

(52) U.S. Cl.
CPC ............ *A45D 19/02* (2013.01); *A61K 8/046* (2013.01); *A61K 8/8147* (2013.01); *A61K 8/8152* (2013.01); *A61K 8/8158* (2013.01); *A61K 8/87* (2013.01); *A61Q 5/06* (2013.01); *B05B 7/0483* (2013.01); *B65D 83/44* (2013.01); *B65D 83/752* (2013.01); *A61K 2800/30* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 3,120,348 A | * | 2/1964 | O'Donnell ............ B05B 1/3436 239/490 |
| 3,137,416 A | | 6/1964 | Shepherd et al. |
| 3,146,922 A | | 9/1964 | Tuttle |
| 3,472,243 A | | 10/1969 | Wall |
| 3,472,604 A | | 10/1969 | Dasher |
| 3,475,114 A | | 10/1969 | Bolinger |
| 3,537,809 A | | 11/1970 | Cednas |
| 3,583,408 A | | 6/1971 | Wall |
| 3,587,942 A | | 6/1971 | Gailitis |
| 3,619,114 A | | 11/1971 | Anzuino et al. |
| 3,619,117 A | | 11/1971 | Anzuino |
| 3,619,118 A | | 11/1971 | Anzuino |
| 3,633,591 A | | 1/1972 | Anzuino |
| 3,634,022 A | | 1/1972 | Robbins et al. |
| 3,661,161 A | | 5/1972 | Kalopissis |
| 3,676,550 A | | 7/1972 | Anzuino |
| 3,678,157 A | | 7/1972 | Kalopissis |
| 3,680,738 A | | 8/1972 | Vos |
| 3,819,090 A | | 6/1974 | Birrell |
| 3,820,550 A | | 6/1974 | Kinney |
| 3,876,168 A | | 4/1975 | Powers, Jr. |

(Continued)

FOREIGN PATENT DOCUMENTS

| | | |
|---|---|---|
| DE | 1935991 U | 3/1966 |
| DE | 3048011 A | 7/1982 |

(Continued)

OTHER PUBLICATIONS

Troy. Remington: The Science and Practice of Pharmacy Baltimore: Lippincott Williams & Wilkins, 2006, p. 1009 (Year: 2006).*

(Continued)

*Primary Examiner* — Robert A Wax
*Assistant Examiner* — Caralynne E Helm
(74) *Attorney, Agent, or Firm* — Alexandra S. Anoff

(57) ABSTRACT

The present invention relates to an aerosol hairspray product. The product comprises: a pressurizable container comprising a container wall which encloses a reservoir for storing a hairstyling formulation and a liquefied gas propellant; and a spraying device attached to the container for dispensing the hairstyling formulation from the reservoir of the container. The spraying device comprises a valve and a nozzle and the valve comprises a valve body, a stem and a spring means. The valve body houses an insert and the insert comprises an insert orifice and at least two channels. The channels are tangentially disposed about the insert orifice. Also the valve body comprises at least two vapor taps. Furthermore the insert orifice is capable of being in liquid communication with the hairstyling formulation in the reservoir.

14 Claims, 4 Drawing Sheets

(56) References Cited

U.S. PATENT DOCUMENTS

| | | | |
|---|---|---|---|
| 3,882,114 A | 5/1975 | Kalopissis | |
| 3,909,195 A | 9/1975 | Machell | |
| 4,152,416 A | 5/1979 | Marra | |
| 4,167,692 A | 9/1979 | Sekiya et al. | |
| 4,257,560 A | 3/1981 | Diamond | |
| 4,278,659 A | 7/1981 | Breuer | |
| 4,338,295 A | 7/1982 | Highley | |
| 4,393,984 A | 7/1983 | Debard | |
| 4,417,674 A * | 11/1983 | Giuffredi | B65D 83/48 222/402.18 |
| 4,588,760 A | 5/1986 | Jachowicz | |
| 4,699,936 A | 10/1987 | Vasta | |
| 4,719,104 A | 1/1988 | Patel | |
| 4,726,945 A | 2/1988 | Patel | |
| 4,801,853 A | 1/1989 | Lewis et al. | |
| 4,890,049 A | 12/1989 | Auinger | |
| 5,002,761 A | 3/1991 | Mueller | |
| 5,068,099 A | 11/1991 | Sramek | |
| 5,068,587 A | 11/1991 | Nakamura et al. | |
| 5,094,364 A | 3/1992 | Knickerbocker | |
| 5,105,988 A | 4/1992 | Knickerbocker | |
| 5,126,124 A | 6/1992 | Tazi et al. | |
| 5,182,098 A | 1/1993 | Kopolow et al. | |
| 5,199,615 A | 4/1993 | Downing | |
| 5,207,785 A | 5/1993 | Knickerbocker | |
| 5,223,247 A | 6/1993 | Kopolow et al. | |
| 5,304,368 A | 4/1994 | Shernov et al. | |
| 5,306,972 A | 4/1994 | Hokanson et al. | |
| 5,348,731 A | 9/1994 | Patti | |
| 5,362,486 A | 11/1994 | Nandagiri | |
| 5,385,303 A | 1/1995 | Gosselin | |
| 5,411,185 A | 5/1995 | Drobish | |
| 5,441,728 A | 8/1995 | Tsaur | |
| 5,458,871 A | 10/1995 | Malawer et al. | |
| 5,462,727 A | 10/1995 | Engler | |
| 5,468,791 A | 11/1995 | Yuan | |
| 5,525,657 A | 6/1996 | Anchor et al. | |
| 5,526,985 A | 6/1996 | Martin | |
| 5,560,544 A | 10/1996 | Merritt | |
| 5,614,799 A | 3/1997 | Anderson et al. | |
| 5,637,296 A | 6/1997 | Rocafort | |
| 5,665,804 A | 9/1997 | Hill | |
| 5,676,311 A | 10/1997 | Hartman | |
| 5,735,465 A | 4/1998 | LaForcade | |
| 5,752,396 A | 5/1998 | Schmid et al. | |
| 5,901,907 A | 5/1999 | Hildebrant | |
| 5,912,522 A | 6/1999 | Rivera | |
| 5,918,774 A | 7/1999 | Lund | |
| 5,927,604 A | 7/1999 | Laidler | |
| 6,000,633 A | 12/1999 | Lund | |
| 6,106,577 A | 8/2000 | Audousset | |
| 6,126,921 A | 10/2000 | Emmerling | |
| 6,136,884 A | 10/2000 | Chen | |
| 6,158,625 A | 12/2000 | Siegel | |
| 6,165,446 A | 12/2000 | Samain | |
| 6,215,261 B1 | 4/2001 | Becerra | |
| 6,223,951 B1 | 5/2001 | Siegel | |
| 6,264,067 B1 | 7/2001 | Lasserre | |
| 6,346,234 B1 | 2/2002 | Rollat | |
| 6,350,439 B1 | 2/2002 | Dupuis | |
| 6,440,404 B1 | 8/2002 | Dupuis | |
| 6,482,808 B1 | 11/2002 | Grasser | |
| 6,495,119 B1 | 12/2002 | Sturla et al. | |
| 6,503,479 B1 | 1/2003 | LesAulnier | |
| 6,509,012 B1 | 1/2003 | Hossel | |
| 6,512,034 B1 | 1/2003 | Hamada et al. | |
| 6,543,703 B2 | 4/2003 | Blake | |
| 6,558,697 B2 | 5/2003 | Cannell | |
| 6,655,552 B2 | 12/2003 | Aiken | |
| 6,727,668 B1 | 4/2004 | Maslov et al. | |
| 6,740,317 B1 | 5/2004 | Cho | |
| 6,852,815 B1 | 2/2005 | Chuang | |
| 6,913,711 B2 | 7/2005 | McKie | |
| 6,966,465 B2 | 11/2005 | Kang | |
| 7,014,127 B2 | 3/2006 | Valpey, III et al. | |
| 7,028,866 B2 | 4/2006 | Kunesh | |
| 7,102,307 B2 | 9/2006 | Shao | |
| 7,169,380 B2 | 1/2007 | Rollat | |
| 7,205,271 B2 | 4/2007 | Drzewinski | |
| 7,255,869 B2 | 8/2007 | Uchida | |
| 7,303,087 B2 | 12/2007 | Flashinski | |
| 7,364,055 B2 | 4/2008 | Yquel | |
| 7,448,517 B2 | 11/2008 | Shieh et al. | |
| 7,452,525 B1 | 11/2008 | Berezkin | |
| 7,487,891 B2 | 2/2009 | Yerby | |
| 7,888,904 B2 | 2/2011 | Mularcik | |
| 7,972,589 B2 | 7/2011 | Leighton | |
| 7,981,167 B2 | 7/2011 | Carballada | |
| 8,048,846 B2 | 11/2011 | Chahal | |
| 8,114,938 B2 | 2/2012 | Berezkin | |
| D658,009 S | 4/2012 | Davis | |
| 8,173,583 B2 | 5/2012 | Castro | |
| 8,241,613 B2 | 8/2012 | Candau | |
| 8,318,879 B2 | 11/2012 | Hashemzadeh | |
| 8,328,120 B2 | 12/2012 | Vanblaere | |
| D681,344 S | 5/2013 | McNeill | |
| 8,440,211 B2 | 5/2013 | Auguste | |
| 8,981,696 B2 | 3/2015 | Bates et al. | |
| 9,259,481 B2 | 2/2016 | Shin et al. | |
| 9,694,087 B2 | 7/2017 | Shin et al. | |
| 2002/0028187 A1 | 3/2002 | Nekludoff et al. | |
| 2002/0125462 A1 | 9/2002 | McKie et al. | |
| 2002/0150542 A1 | 10/2002 | Steinmetz et al. | |
| 2002/0176834 A1 | 11/2002 | Adams | |
| 2003/0082223 A1 * | 5/2003 | Healy | A61K 8/046 424/401 |
| 2003/0103930 A1 | 6/2003 | Uchida | |
| 2003/0106901 A1 | 6/2003 | Meshberg | |
| 2003/0175229 A1 | 9/2003 | Giroud | |
| 2003/0215399 A1 | 11/2003 | Smith | |
| 2003/0215400 A1 | 11/2003 | Schroeder | |
| 2004/0013615 A1 | 1/2004 | Dubief | |
| 2004/0016062 A1 | 1/2004 | Plos | |
| 2004/0042974 A1 | 3/2004 | Dupuis et al. | |
| 2004/0115151 A1 | 6/2004 | Giroud | |
| 2004/0136921 A1 | 7/2004 | Schulz et al. | |
| 2004/0144863 A1 * | 7/2004 | Kendrick | B65D 83/752 239/337 |
| 2004/0166071 A1 | 8/2004 | Pfaffernoschke | |
| 2004/0245294 A1 | 12/2004 | Mineau | |
| 2004/0261198 A1 | 12/2004 | Kainz | |
| 2005/0023368 A1 | 2/2005 | Valpey, III et al. | |
| 2005/0052080 A1 | 3/2005 | Maslov et al. | |
| 2006/0060554 A1 | 3/2006 | Garman | |
| 2006/0076171 A1 | 4/2006 | Donnelly et al. | |
| 2006/0105003 A9 | 5/2006 | Rollat-Corvol | |
| 2007/0018017 A1 | 1/2007 | Tilton | |
| 2007/0066506 A1 | 3/2007 | Behler | |
| 2007/0241132 A1 | 10/2007 | Smith | |
| 2007/0245538 A1 | 10/2007 | Salameh | |
| 2007/0267447 A1 | 11/2007 | Kennedy | |
| 2007/0275020 A1 | 11/2007 | Lendlein | |
| 2007/0277332 A1 | 12/2007 | Bimczok | |
| 2007/0286833 A1 | 12/2007 | Keller | |
| 2007/0292641 A1 | 12/2007 | Altonen | |
| 2008/0003387 A1 | 1/2008 | Altonen | |
| 2008/0017666 A1 | 1/2008 | Vanblaere | |
| 2008/0020004 A1 | 1/2008 | Birkel | |
| 2008/0035638 A1 | 2/2008 | Burghaus | |
| 2008/0041884 A1 | 2/2008 | Chevalier | |
| 2008/0102051 A1 | 5/2008 | Huynh | |
| 2008/0112591 A1 | 5/2008 | Schiemann et al. | |
| 2008/0116759 A1 | 5/2008 | Lin | |
| 2008/0152610 A1 * | 6/2008 | Cajan | A61K 8/046 424/70.9 |
| 2008/0166305 A1 | 7/2008 | Singh et al. | |
| 2008/0187505 A1 | 8/2008 | Speckbacher | |
| 2008/0187506 A1 | 8/2008 | Carballada | |
| 2008/0197152 A1 | 8/2008 | Neuhaus | |
| 2008/0210253 A1 | 9/2008 | Carballada | |
| 2008/0219934 A1 | 9/2008 | Kim | |
| 2008/0279804 A1 | 11/2008 | Parker | |
| 2008/0311050 A1 | 12/2008 | Lendlein | |
| 2009/0010865 A1 | 1/2009 | Kim | |

(56) References Cited

U.S. PATENT DOCUMENTS

| | | | |
|---|---|---|---|
| 2009/0022681 | A1 | 1/2009 | Carballada |
| 2009/0041689 | A1 | 2/2009 | Berezkin |
| 2009/0050599 | A1 | 2/2009 | Martin |
| 2009/0050634 | A1 | 2/2009 | Girardot |
| 2009/0050638 | A1 | 2/2009 | Smith |
| 2009/0060858 | A1 | 3/2009 | Schwarzwaelder |
| 2009/0060859 | A1 | 3/2009 | Castro |
| 2009/0074697 | A1 | 3/2009 | Huynh |
| 2009/0084870 | A1 | 4/2009 | Smith |
| 2009/0084872 | A1 | 4/2009 | Vanblaere |
| 2009/0104138 | A1 | 4/2009 | Shimatani |
| 2009/0118044 | A1 | 5/2009 | Kuo |
| 2009/0124961 | A1* | 5/2009 | Harman .............. A61K 9/122 604/24 |
| 2009/0160392 | A1 | 6/2009 | Mularcik |
| 2009/0295315 | A1 | 12/2009 | Tarnow et al. |
| 2009/0297467 | A1 | 12/2009 | Laurent |
| 2010/0028286 | A1 | 2/2010 | Carballada |
| 2010/0052584 | A1 | 3/2010 | Bates et al. |
| 2010/0116909 | A1 | 5/2010 | Abduljalil |
| 2010/0123426 | A1 | 5/2010 | Nashiki et al. |
| 2010/0135917 | A1 | 6/2010 | Winter |
| 2010/0189664 | A1 | 7/2010 | Castro |
| 2011/0027211 | A1 | 2/2011 | Viala |
| 2011/0064684 | A1 | 3/2011 | Krause |
| 2011/0114759 | A1 | 5/2011 | Schmitz |
| 2011/0158928 | A1* | 6/2011 | Mueller ............ A61K 8/8129 424/70.15 |
| 2011/0192415 | A1 | 8/2011 | Verboom et al. |
| 2011/0205662 | A1 | 8/2011 | Bates et al. |
| 2011/0241592 | A1 | 10/2011 | Lin |
| 2011/0303766 | A1 | 12/2011 | Smith |
| 2011/0303767 | A1 | 12/2011 | Smith |
| 2012/0031419 | A1 | 2/2012 | Batt |
| 2012/0034173 | A1 | 2/2012 | Batt |
| 2012/0111898 | A1 | 5/2012 | Neuhaus |
| 2012/0180807 | A1 | 7/2012 | Flohr |
| 2012/0183486 | A1 | 7/2012 | Flohr |
| 2012/0263669 | A1* | 10/2012 | Mueller .............. A61K 8/046 424/70.15 |
| 2013/0058882 | A1 | 3/2013 | Flohr |
| 2013/0068243 | A1 | 3/2013 | Birkel |
| 2013/0068849 | A1 | 3/2013 | Birkel et al. |
| 2014/0070025 | A1 | 3/2014 | Dalbo |
| 2015/0000687 | A1 | 1/2015 | Brown et al. |
| 2015/0004200 | A1 | 1/2015 | Brown et al. |
| 2015/0232260 | A1 | 8/2015 | Dann et al. |
| 2016/0175238 | A1 | 6/2016 | Shin et al. |
| 2016/0250120 | A1 | 9/2016 | Knappe et al. |
| 2016/0263009 | A1 | 9/2016 | Saito et al. |
| 2016/0303023 | A1 | 10/2016 | Bevinakatti |
| 2016/0346175 | A1 | 12/2016 | Sasik et al. |
| 2016/0347536 | A1 | 12/2016 | Brown et al. |

FOREIGN PATENT DOCUMENTS

| | | |
|---|---|---|
| DE | 4121834 A1 | 1/1993 |
| DE | 4431577 A1 | 3/1996 |
| DE | 29615896 U1 | 1/1998 |
| DE | 10259199 A1 | 6/2004 |
| DE | 102004036004 A1 | 2/2006 |
| DE | 102005018205 A1 | 10/2006 |
| DE | 102008024650 A1 | 4/2010 |
| EP | 0379627 A1 | 8/1990 |
| EP | 0574607 A1 | 12/1993 |
| EP | 0471054 B1 | 5/1994 |
| EP | 0688577 A1 | 12/1995 |
| EP | 0644750 B1 | 4/1996 |
| EP | 0618793 B1 | 5/1997 |
| EP | 0696545 B1 | 6/1999 |
| EP | 1026220 A1 | 8/2000 |
| EP | 0151973 A2 | 7/2001 |
| EP | 0873946 B1 | 7/2001 |
| EP | 0758222 B1 | 8/2001 |
| EP | 0791351 B1 | 12/2002 |
| EP | 1220956 B1 | 7/2003 |
| EP | 0832639 B1 | 1/2004 |
| EP | 1161934 B1 | 4/2004 |
| EP | 1092650 B1 | 12/2005 |
| EP | 1160178 B1 | 7/2006 |
| EP | 1681078 B1 | 12/2008 |
| EP | 1719500 B1 | 6/2010 |
| EP | 2407145 A1 | 1/2012 |
| EP | 2228319 B1 | 5/2013 |
| FR | 2784081 B1 | 4/2000 |
| JP | H0454116 A | 2/1992 |
| JP | H04208214 A | 7/1992 |
| JP | H10279436 A | 10/1998 |
| JP | 10337509 A | 12/1998 |
| JP | 11076881 A | 3/1999 |
| JP | 11228398 A * | 8/1999 |
| JP | 2001227475 A | 8/2001 |
| JP | 2002347866 A | 12/2002 |
| JP | 2003054668 A | 2/2003 |
| JP | 2004195287 | 7/2004 |
| JP | 3727112 B2 | 12/2005 |
| JP | 3828257 B2 | 10/2006 |
| JP | 2007117940 A | 5/2007 |
| JP | 3969517 B2 | 9/2007 |
| JP | 2007296428 A | 11/2007 |
| JP | 4278878 B2 | 6/2009 |
| JP | 2011-190195 A | 9/2011 |
| WO | WO9725259 A1 | 7/1997 |
| WO | WO9729029 A1 | 8/1997 |
| WO | WO9800354 A1 | 1/1998 |
| WO | WO9967216 A1 | 12/1999 |
| WO | WO200045777 A1 | 8/2000 |
| WO | WO200153157 A2 | 7/2001 |
| WO | WO0170179 A1 | 9/2001 |
| WO | WO200213773 A2 | 2/2002 |
| WO | WO200245665 A1 | 6/2002 |
| WO | WO03061839 A1 | 7/2003 |
| WO | WO2004043330 A2 | 5/2004 |
| WO | WO2004062633 A1 | 7/2004 |
| WO | WO2007099268 A2 | 9/2007 |
| WO | WO2007099269 A2 | 9/2007 |
| WO | WO2007099271 A2 | 9/2007 |
| WO | WO 2012009302 A1 * | 1/2012 ............ A61K 8/046 |

OTHER PUBLICATIONS

Miao Wang; Acrylates/Hydroxyesters Acrylates Copolymer in Personal Care Applications: Acudyne DHR Durable Hold Resin; RD478006; Feb. 10, 2004.

Andrea Keenan; Hair Styling Formulations Containing Acudyne 180 Hair Fixative Polymer and Aculyn Rheology Modifiers; RD478088; Feb. 10, 2004.

Miao Wang; Mousse Formulations Containing Acudyne DHR or Acudyne 180 Hair Fixative Polymer and Aculyn 88 Rheology Modifier; RD510027; Oct. 10, 2006.

PCT International Search Report for PCT/US2014/044332 dated Dec. 23, 2014, 10 pages.

PCT International Search Report for PCT/US2014/044339 dated Jan. 22, 2015, 14 pages.

Product introduction: inserts [online], by Precision Valve Japan, Ltd, 2006 [Searching date: Jun. 22, 2016] <URL: http://pvj.co.jp/lv2/index.php?>.

All final and non-final office actions for U.S. Appl. No. 13/180,931.
All final and non-final office actions for U.S. Appl. No. 13/181,058.
All final and non-final office actions for U.S. Appl. No. 13/614,249.
All final and non-final office actions for U.S. Appl. No. 13/614,925.
All final and non-final office actions for U.S. Appl. No. 14/315,917.
All final and non-final office actions for U.S. Appl. No. 15/170,031.

CAS Registry entry for 1,2-difluoroethane, 2014.
CAS Registry entry for dimethyl ether, 2014.

PCT International Search Report and Written Opinion for PCT/US2016/035210 dated Jul. 28, 2016, 13 pages.

Philip M. Cook; Low VOC Hairsprays—It Depends Very Much on the Choice of Polymer—XP009146664 (CM3554FMQ Extended EPSR.

(56) References Cited

OTHER PUBLICATIONS

Product introduction: inserts [online], by Precision Valve Japan, Ltd, 2006 [Searching date: Jun. 22, 2016] <URL: http://ovj.co.jp/lv2/index.php?>.

"The Shellac Story—Shellac Properties", retrieved from the internet: http://www.shellac.in.shellac_properties.html, retrieved on Jul. 11, 2011.

* cited by examiner

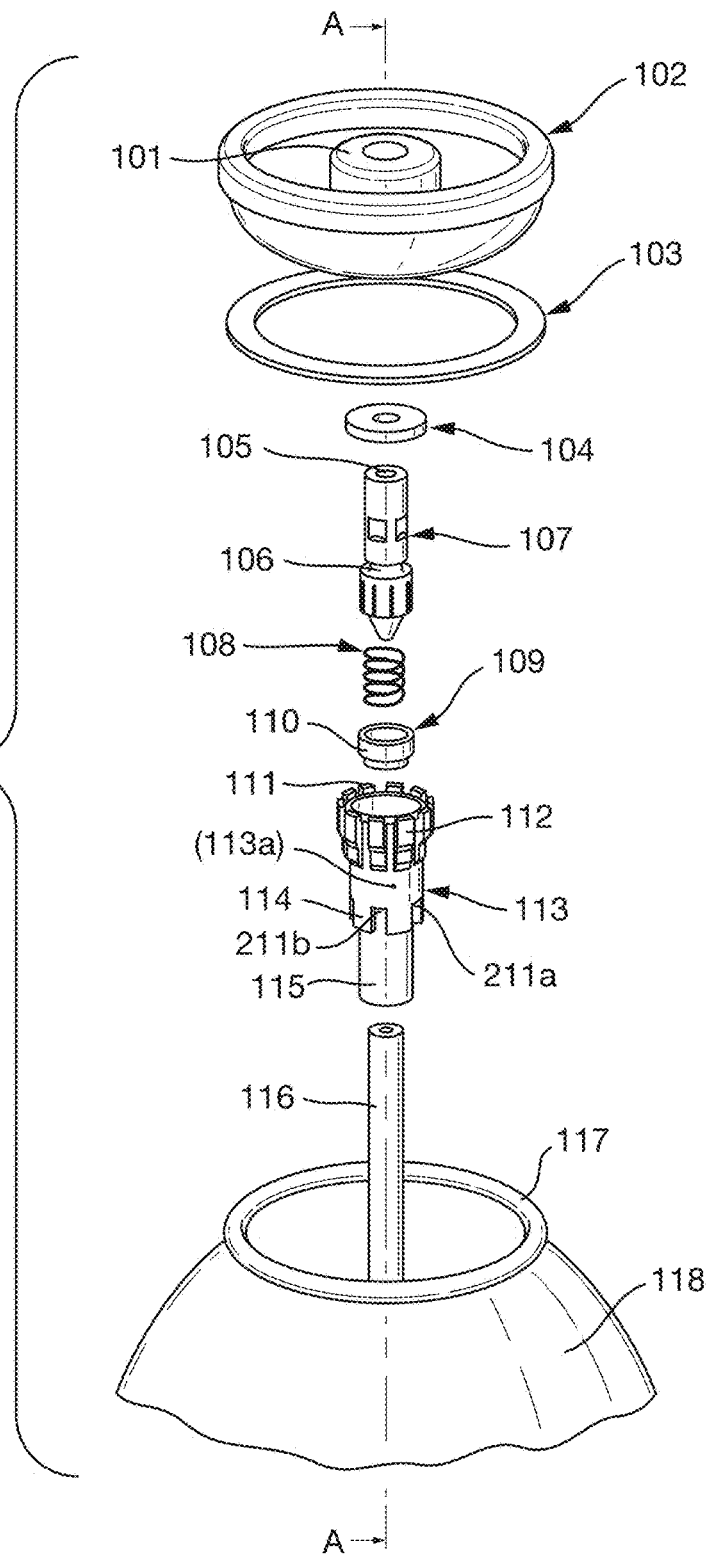

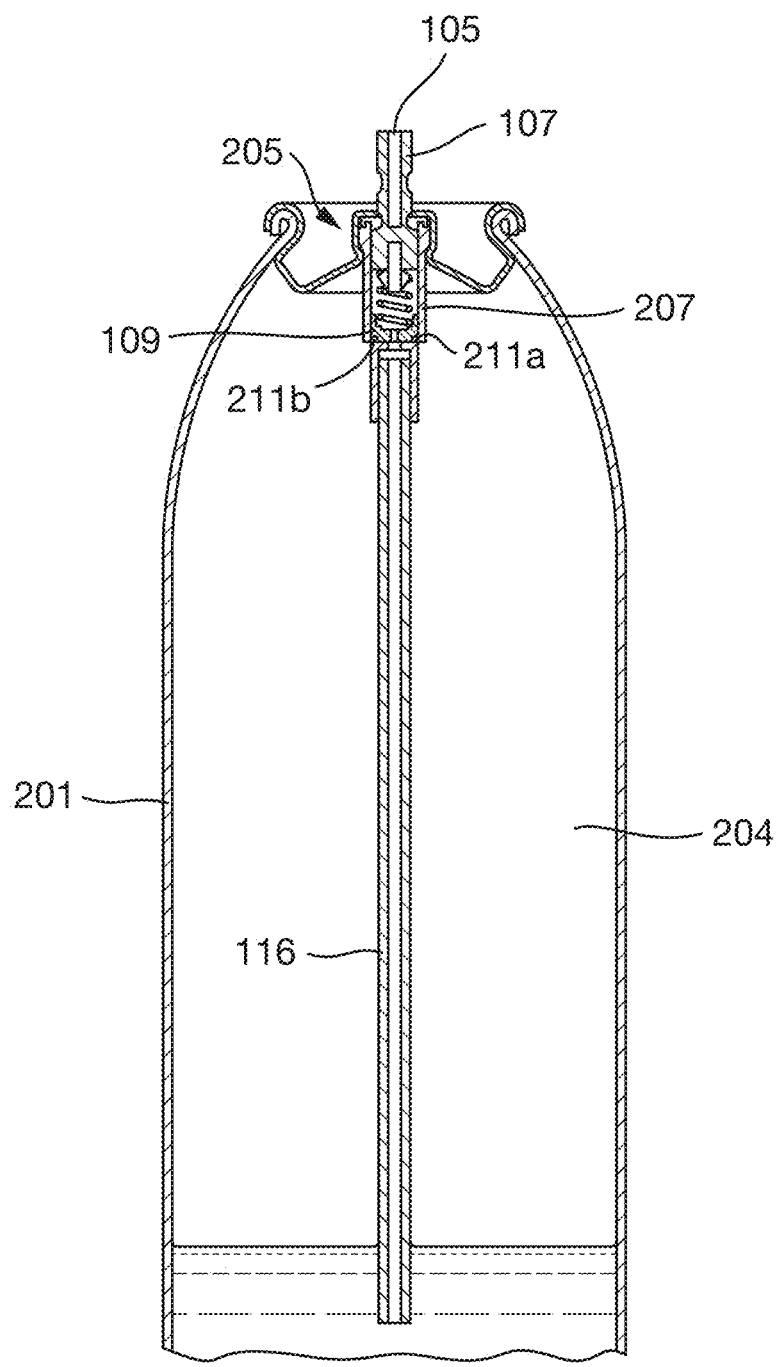

AEROSOL HAIRSPRAY PRODUCT COMPRISING A SPRAYING DEVICE

FIELD OF THE INVENTION

An aerosol hairspray product wherein the product comprises: a pressurisable container 118 comprising a container wall 201 which encloses a reservoir 204 for storing a hairstyling formulation and a liquefied gas propellant; and a spraying device attached to the container 118 for dispensing the hairstyling formulation from the reservoir 204 of the container 118, wherein the spraying device comprises a valve 205 and a nozzle, wherein the valve comprises a valve body 113, a stem 107 and a spring means 108, and wherein the valve body 113 houses an insert 109, and wherein the insert comprises an insert orifice 109*a* and at least two channels 110*a*, 110*b*, wherein the channels 110*a*, 110*b* are tangentially disposed about the insert orifice 109*a*, and wherein the valve body 113 comprises at least two vapour taps 211*a*, 211*b*, and wherein the insert orifice 109*a* is capable of being in liquid communication with the hairstyling formulation in the reservoir 204.

BACKGROUND OF THE INVENTION

Hairstyling products such as hairsprays are used for achieving different hairstyles and for holding hair strands in place for a period of time. Typically, hairsprays comprise film-forming polymers, which when applied to keratin-containing fibres, such as human hair, form fibre-fibre welds. These welds 'glue' the fibres together and hence impart hold to the hairstyle.

Aerosol hairspray products usually comprise a pressure-resistant container, a nozzle, a propellant, and a hairstyling formulation. A hairspray composition is normally ejected from such products via aerosol-forming nozzle. See, for example, US2009/0104138A1. Alcohols are normally used in the hairstyling formulation, for example to reduce surface tension. However, a high proportion of alcohol may leave the hair feeling dry and brittle and some alcohols may cause an allergic response in some users. In addition ethanol is a VOC, volatile organic compound, which can accumulate in the environment and cause environmental concerns. Also, ethanol is flammable.

Shernov et al in U.S. Pat. No. 5,304,368A ("Shernov", hereinafter) relates to a non-foaming, non-viscous, alcohol-free, water-based pressurized hair-fixative spray product for use as the total fill in an aerosol container by delivery from an actuated-valve of predetermined dimensions, particularly the vapor tap and stem orifice sizes. Birkel et al in US2013/0068849A1 ("Birkel", hereinafter) relates to an aerosol hairspray product for styling and/or shaping hair wherein the product comprises: a container; a spraying device; a propellant; a hairstyling formulation comprising: (a) at least about 50% water; and (b) from about 0.01% to about 20% of a hairstyling polymer, wherein the hairstyling polymer is selected from the group consisting of: acrylates copolymers of two or more monomers of (meth)acrylic acid or one of their simple esters; acrylateslhydroxyesters acrylates copolymers of butyl acrylate, methyl methacrylate, methacrylic acid, ethyl acrylate and hydroxyethyl methacrylate; polyurethane-14/AMP-acrylates polymer blend; and mixtures thereof. Harman in US2009/0124961A1 ("Harman", hereinafter) relates to a steam-sterilizable aerosol valve [that] has a valve body of polymeric material such as polyphenylene sulfone (PPSU) having an HDT (heat deflection temperature) at 1.8 MPa stress in the range of 200-275° C.

There is a constant need, therefore, for more environmentally friendly, more sustainable, less harsh and more affordable hairspray products. However, altering one or more features of an aerosol hairspray product can be challenging since the interrelationship therebetween affects the product performance. For example, utilising a different propellant may result in an unacceptable decrease in package operating pressure resulting in an increased product wetness on application, drying time and particle size distribution and consequently unsatisfactory hold.

When considering the aforementioned needs when designing such improved hairsprays, therefore, good hairspray performance should be maintained. Performance benefits may include, for example: excellent hold; long-lasting hold; good humidity resistance; shapeable hold; acceptable drying time; excellent soft, natural hair feel; acceptable and/or non-stickiness/tackiness of the hands and hair. Of particular relevance to consumers is excellent hold without stickiness and an acceptable drying time.

SUMMARY OF THE INVENTION

According to a first aspect, the present invention relates to an aerosol hairspray product wherein the product comprises:

i. a pressurisable container 118 comprising a container wall 201 which encloses a reservoir 204 for storing a hairstyling formulation and a liquefied gas propellant;

ii. the hairstyling formulation comprising:

(a) from about 30% to about 60% water, by total weight of the hairstyling formulation and propellant; and (b) from about 5.0% to about 15% hairstyling polymer by total weight of the hairstyling formulation and propellant, wherein the hairstyling polymer is water-soluble; and (c) less than about 2% alcohol, by total weight of the hairstyling formulation and propellant, preferably substantially free of alcohol;

iii. a spraying device attached to the container 118 for dispensing the hairstyling formulation from the reservoir 204 of the container 118, wherein the spraying device comprises a valve 205 and a nozzle, wherein the valve comprises a valve body 113, a stem 107 and a spring means 108, and wherein the valve body 113 houses an insert 109, and wherein the insert comprises an insert orifice 109*a* and at least two channels 110*a*, 110*b*, wherein the channels 110*a*, 110*b* are tangentially disposed about the insert orifice 109*a*, and wherein the valve body 113 comprises at least two vapour taps 211*a*, 211*b*, and wherein the insert orifice 109*a* is capable of being in liquid communication with the hairstyling formulation in the reservoir 204.

According to a second aspect, the present invention relates to use the of the product according to the first aspect for styling hair.

According to a third aspect, the present invention relates to a method of styling hair comprising:

i. providing the product according to the first aspect; and ii. causing the product to spray at a delivery rate, wherein the delivery rate is from about 0.25 g/sec to about 0.45 g/sec; and wherein an ejected composition is sprayed, wherein the ejected composition comprises particles having an average particle size distribution (Dv50) of at least about 35 micron.

BRIEF DESCRIPTION OF THE DRAWINGS
List of reference signs 101. pedestal of mounting cup
102. mounting cup
103. cup gasket
104. stem gasket
105. stem orifice
106. seat for the stem gasket
107. stem (stem valve)
108. spring means
109. insert
109a. insert orifice
110a, 110b. channels
110. bottom of the insert
111. valve housing ridge
112. castellation area
113. valve body
113a. vapour housing hole
114. external slots
115. valve tailpiece
116. dip tube
118. container
204. reservoir
205. valve
207. housing
211a, 211b. vapour taps (gas receiving holes)

FIG. 1: shows an exploded diagram of an aerosol valve in situ.

FIG. 3: shows the valve clinched on to the container.

DETAILED DESCRIPTION OF THE INVENTION

Definitions and General

Figure 2A:
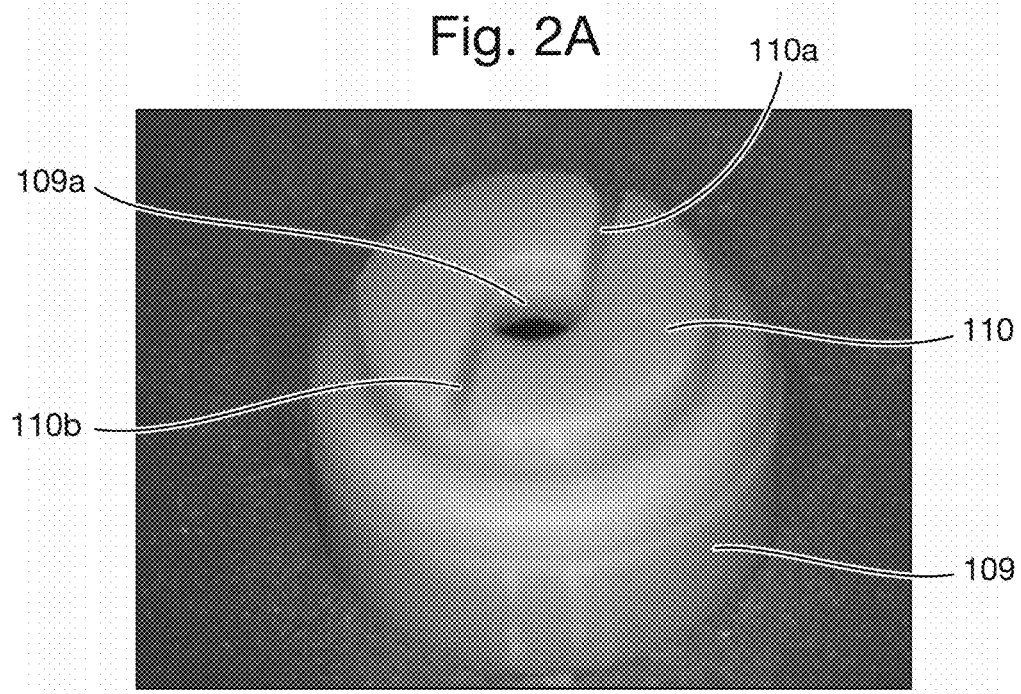
FIG. 2A: shows the underside of insert such that the channels can be clearly seen.

In all embodiments of the present invention, all percentages are by weight of the total composition (or formulation), unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about 1 atmosphere of pressure and at about 50% relative humidity. All such weights as they pertain to listed ingredients are based on the active level and do not include carriers or by-products that may be included in commercially available materials, unless otherwise specified. The unit "g" means grams. The unit "micron" means micrometer. "QS" or "QSP" means sufficient quantity for 100%. +/− indicates the standard deviation. 0.01 inch=0.254 mm and 1 mm=0.039 inch (in case of contradiction, the measurement in inches is decisive).

Herein, "comprising" means that other steps and other ingredients which do not affect the end result can be added. This term encompasses the terms "consisting of" and "consisting essentially of". The compositions, methods, uses, kits, and processes of the present invention can comprise, consist of, and consist essentially of the elements and limitations of the invention described herein, as well as any of the additional or optional ingredients, components, steps, or limitations described herein.

Where amount ranges are given, these normally relate to the total amount of the (class of) compound(s) specified. For example, "the composition comprises from about 0.1% to about 20% of ethylenic monomer" means that the total amount of ethylenic monomer (including mixtures of different such monomers) in the composition must be within the specified range.

The term "substantially free from" or "substantially free of" as used herein means less than about 1%, less than about 0.8%, less than about 0.5%, less than about 0.3%, or about 0%, by total weight of the composition or formulation.

"Hair," as used herein, means mammalian hair including scalp hair, facial hair and body hair, more preferably hair on the human head and scalp. "Hair shaft" means an individual hair strand and may be used interchangeably with the term "hair."

"Cosmetically acceptable," as used herein, means that the compositions, formulations or components described are suitable for use in contact with human keratinous tissue without undue toxicity, incompatibility, instability, allergic response, and the like. All compositions and formulations described herein which have the purpose of being directly applied to keratinous tissue are limited to those being cosmetically acceptable.

"Derivatives," as used herein, includes but is not limited to, amide, ether, ester, amino, carboxyl, acetyl, acid, salt and/or alcohol derivatives of a given compound.

"Monomer," as used herein, means a discrete, non-polymerised chemical moiety capable of undergoing polymerisation in the presence of an initiator. "Ethylenic monomer," as used herein, means a chemical species that contains an olefinic carbon-carbon double bond (C=C) and is capable of undergoing polymerization in the presence of an initiator.

"Polymer," as used herein, means a chemical formed from the polymerisation of two or more monomers. The term "polymer" as used herein shall include all materials made by the polymerisation of monomers as well as natural polymers. Polymers made from only one type of monomer are called homopolymers. A polymer comprises at least two monomers. Polymers made from two or more different types of monomers are called copolymers. The distribution of the different monomers can be calculated statistically or block-wise—both possibilities are suitable for the present invention. Except if stated otherwise, the term "polymer" used herein includes any type of polymer including homopolymers and copolymers.

The term "water-soluble" as used herein refers to any material that is sufficiently soluble in water to form a single-phase solution to the naked eye at a concentration of 0.1% by weight of the material in water at 25° C. It may be necessary to adjust the pH of the mixture or fully neutralize the mixture after addition of the material to water to achieve the water solubility. These methods are well-known, for example, in the water-soluble hairstyling polymer applications industry and are typically instructed with the supplied material sample. Water-solubility is typically measured by the following protocol: 0.1% by weight of the material is added to distilled water at 25° C. and the pH adjusted/neutraliser added as needed. This is stirred vigorously on a magnetic stirrer set at 600 rpm, for 30 minutes. The solution is then allowed to settle for 1 hour and the number of phases observed by the naked eye. For example, where any solid material can be seen in an otherwise single-phase solution, then this is considered to be two phases.

The term "water-insoluble" as used herein refers to any material that is not "water-soluble".

The term "molecular weight" or "M·Wt." as used herein refers to the number average molecular weight unless otherwise stated.

"Kit," as used herein, means a packaging unit comprising a plurality of components i.e. a kit of parts. An example of a kit is, for example, a first composition and a separately packaged second composition. Another kit may comprise application instructions comprising a method and a composition/formulation.

Embodments and aspects described herein may comprise or be combinable with elements or components of other embodiments and/or aspects despite not being expressly exemplified in combination, unless otherwise stated or an incompatibility is stated.

Explanation of the Invention

Hairspray consumers and professional stylists have only alcohol-based hairsprays available to them that have acceptable performance. The benefits of very low alcohol or alcohol-free hairsprays, as provided by the present invention, include purer fragrance (in view of the absence of an alcohol smell), less observed hair dryness and reduced brittleness effects to the hair. Moreover, such hairsprays are safer, more environmentally friendly, and healthier to use. The inventors have tailored the hairspray of the present invention such that these new benefits do not provide any drawbacks versus the key benefits of a hairspray expected by the consumer and stylist, which include initial and long-lasting hold, non-sticky and natural hair look and feel, and maintenance of the desired initial hairstyle without overwetting the hair with the ejected composition and causing it to be weighed down. It is difficult to balance over-wetting from the hairspray application with applying enough hairstyling (i.e. film-forming) polymer, which is the styling active to provide initial and long-lasting hold. This is a significantly lesser problem with alcohol-based hairsprays as the alcohol evaporates quickly in air. Therefore, for very low alcohol or alcohol-free hairspray development it is a unique combination of formulation and spray properties that can achieve this balance.

In order to provide similar hold levels as compared to the alcohol-based hairsprays consumers and stylists are used to, the inventors have surprisingly found that it is key to deliver the same range of hairstyling polymer amount onto the hair as alcohol-based hairsprays, and at the same time deliver less total ejected composition to the hair to avoid over-wetting or having unacceptably long drying times because of the presence of high levels of water instead of volatile alcohol in the hairstyling formulation. This problem is new in the field of hairsprays since alcohol-free hairsprays are rare, especially those with proven and reliable performance, particularly over can lifetime. The inventors have found that overall weight of water delivered to the hair is key to the hairspray performance. Too much water causes unacceptably slow dry times and over-wetting which can disrupt the internal ionic interactions of the hair allowing the hair to relax and lose the desired style. Typical alcohol-based hairsprays deliver anywhere between 3% and 40% water as a percentage by weight of the total amount of composition ejected. The hairsprays of this invention being very low alcohol or alcohol-free may deliver circa between 30% to 60% water of the total amount of composition ejected, therefore the total water amount delivered to the hair must be managed by the lower spray rate specified herein. The inventors have found that excellent performance can be achieved for a water-based hairspray by optimizing the hairstyling polymer level in the hairstyling formulation and the viscosity of the hairstyling formulation to achieve certain spray properties—particularly delivery rate and particle size distribution. The research program of the inventors delimited an area within which water-based hairsprays should fall in order to achieve excellent performance that is accepted by the consumer and stylist.

It is unnecessary in the alcohol-based hairspray world to go up to high polymer levels in the finished product to deliver hold because a high amount of polymer can be delivered to hair by increasing the delivery rate without adversely over-wetting hair. Indeed, there is a bias in the literature that excellent hold can only be achieved in the context of an alcohol-based solvent. Thus, the invention disclosed herein is a complex balance since the literature on alcohol-based hairsprays cannot be re-applied to water-based hairsprays. In the hairspray formulations of this invention, the same levels of hold-providing i.e. hairstyling polymer(s) are delivered to the hair with the present invention's delivery rate and particle size distribution that maintains the expected initial hold, dry time and hair feel as a traditional alcohol-based hairspray via the specific combination of the formula polymer level delivered through particular spray properties that delivers less overall amount of spray (especially the water solvent) to the hair, thus still maintaining a similar economic value to the consumer.

The details of the features and preferred features of the invention are described hereinafter. The below descriptions apply to and are suitable for the first and other aspects of the invention mutatis mutandis.

Product

According to the first aspect, the invention relates to an aerosol hairspray product. The product relates to an aerosol hairspray product comprising: a container comprising a reservoir for a hairstyling formulation and a liquefied gas propellant, and a spraying device attached to the container. In at least one embodiment, the product comprises from about 50% to about 65% hairstyling formulation, or from about 55% to about 60% hairstyling formulation, by total weight of the hairstyling formulation and propellant. In at least one embodiment, the product comprises from about 35% to about 50% propellant, or from about 40% to about 45% propellant, by total weight of the hairstyling formulation and propellant. As used herein, albeit unless otherwise stated, details of the hairstyling formulation refers to the formulation before it is placed into the container whereupon it will mix to an extent with the propellant since the propellant is a liquefied gas propellant. The same is true where details of the propellant are mentioned, unless otherwise stated.

The product is an aerosol hairspray product and thus does not include mousse products or any pump spray products.

In at least one embodiment, the aerosol hairspray product is for spraying an ejected composition wherein the ejected composition consists of particles having an average particle size distribution (Dv50) of from 40 micron to 100 micron, or from about 60 micron to about 90 micron. In at least one embodiment, the aerosol hairspray product is for spraying at a delivery rate, wherein the delivery rate is from about 0.25 g/sec, or from about 28 g/sec to about 0.45 g/sec.

Hairstyling Formulation

The product comprises a hairstyling formulation. The hairstyling formulation comprises less than about 2% alcohol, by total weight of the hairstyling formulation and propellant, or is substantially free of alcohol. In at least one embodiment, the hairstyling formulation is substantially free of ethanol, isopropanol and propanol. In at least one embodiment, the hairstyling formulation comprises about 1.8% or less, or about 1.5% or less, or about 1% or less, alcohol by total weight of the hairstyling formulation and propellant. In at least one embodiment, hairstyling formulation comprises about 1.8% or less, or about 1.5% or less, or about 1% or less, aliphatic alcohol by total weight of the hairstyling formulation and propellant. "Aliphatic alcohol" as used herein means an alcohol comprising no aromatic group. The amount of alcohol is important because anything above very low levels of alcohol may leave the hair feeling dry and brittle and some alcohols may cause an allergic response in some users. In addition, aerosol products containing ethanol can have environmental concerns: ethanol, for example, is a VOC. Also alcohols can have safety concerns: ethanol, for example, is flammable.

Viscosity

In at least one embodiment, the hairstyling formulation without propellant has a kinematic viscosity of about 6 cSt or less, wherein the viscosity is measured at 20° C.+/−0.1° C. The kinematic viscosity can be important because when the hairstyling formulation is too viscous then the hairstyling formulation is too thick and cannot be sprayed and/or is clogging—non-homogeneous ejected composition results e.g. irregular spray beam, "spitting" rather than spraying, and/or ejection of lumps. Kinematic viscosity is measured by Ubbelohde tube. Kinematic viscosity is a measure of the resistance to flow of a fluid, equal to its absolute viscosity divided by its density. The SI unit of kinematic viscosity is $m^2 \cdot s^{-1}$. The cgs (centimeters/grams/seconds) physical unit for kinematic viscosity is the stokes (St), which can be expressed in terms of centistokes (cSt). 1 cSt=1 $mm^2 \cdot s^{-1} = 10^{-6}$ $m^2 \cdot s^{-1}$. Water at 20° C. has a kinematic viscosity of about 1 cSt. A Ubbelohde tube is a viscometer for measurement of kinematic viscosity of transparent Newtonian liquids by suspended level principle as described in ASTM D 445 and D 446, and ISO 3104 and 3105. For the Ubbelohde tube measure, there is no temperature effect on results, for other kinematic viscometers, temperatures different from specified test range can affect result. Herein, measurements were taken at a temperature of 20° C.+/−0.1° C. This method can be used to measure from about 0.6 cSt to 100 cSt. For instructions for the use of the Ubbelohde viscometer see ASTM D 445. Use Ubbelohde tube size 0 C for viscosities from 0.6 to 3 cSt at 20° C.+/−0.1° C. Use Ubbelohde tube size 1 for viscosities from 2 to 10 cSt at 20° C.+/−0.1° C. ASTM D445 is the "Standard Test Method for Kinematic Viscosity of Transparent and Opaque Liquids". ASTM D446 is "Specifications and Operating Instructions for Glass Capillary Kinematic Viscometers".

In at least one embodiment, the kinematic viscosity of the hairstyling formulation without propellant is from about 0.5 cSt, or from about 1 cSt, or from about 1.25 cSt, or from about 1.5 cSt, or from about 1.75 cSt, or from about 1.8 cSt to about 5.5 cSt, to about 5 cSt, or to about 4.5 cSt, or to about 4 cSt, or to about 3.5 cSt, or to about 3 cSt, or to about 2.5 cSt, or to about 2.3 cSt, or to about 2.2 cSt, or to about 2.1 cSt, or to about 2.0 cSt.

Delivery Rate

In at least one embodiment, the delivery rate is 0.25 g/sec to about 0.45 g/sec. The delivery rate of the aerosol hairspray product herein is determined following ASTM D 3069-94, "Standard Test Method for Delivery Rate of Aerosol Products." In this test, the delivery rate of the product is determined by measuring the mass lost in a given time period. This correlates with the quantity of material expelled though the valve and actuator combination in a given time period. In this case, the can is tested at room temperature (at 21° C.) and a duration of 2 sec to 10 sec for the actuation time. The delivery rate is then determined by the equation:

Delivery Rate (g/sec)=Mass loss (g)/Actuation time (sec)

If the delivery rate is greater than about 0.45 g/sec, then the on-hair drying time will be too long for consumer satisfaction. This is unique for the water-based hairsprays of this invention as compared to traditional alcohol-based hairsprays, typically traditional hairsprays containing volatile alcohol have delivery rates between about 0.55 g/sec to 0.85 g/sec. Delivery rate can typically be adjusted by altering the pressure inside the container (increased pressure correlates with faster delivery rate) and/or the orifices in the spraying device, such as the orifices in the nozzle, orifices in the valve, and the inner diameter of the dip tube. Typically lower diameter correlates with slower delivery rate. In addition, the amount of ejected composition delivered to the hair can also be adjusted by varying the hairstyling formulation to propellant ratio. Increasing the amount of propellant versus hairstyling formulation will result in a spray that has a higher propellant delivery rate and lower product spray rate because the propellant has a lower density than the formulation. In at least one embodiment, the delivery rate is from about 0.26 g/sec, or from about 0.27 g/sec, or from about 0.28 g/sec, or from about 0.29 g/sec, or from about 0.30 g/sec, or from about 0.31 g/sec, or from about 0.32 g/sec, or from about 0.33 g/sec, or from about 0.34 g/sec, or from about 0.35 g/sec, or from about 0.36 g/sec, or from about 0.37 g/sec, or from about 0.38 g/sec, or from about 0.39 g/sec, or from about 0.40 g/sec to about 0.44 g/sec, or to about 0.43 g/sec, to about 0.42 g/sec, to about 0.41 g/sec, or to about 0.40 g/sec, or to about 0.39 g/sec, or to about 0.38 g/sec.

Particle Size Distribution

In at least one embodiment, an ejected composition is sprayed. The ejected composition comprises/consists of particles having an average particle size distribution (Dv50) of at least about 35 micron. The particles are droplets comprising the hairstyling formulation. The average particle size distribution (Dv50) is important in view of ejected composition drying time, which must be consumer acceptable. Indeed, a smaller average particle size distribution (Dv50) is useful in that more particles have a higher surface area to volume ratio, which means a faster drying time. On the other hand, a too low average particle size distribution (Dv50) means that not enough hairstyling polymer is provided to the hair to provide spot welds. A Malvern Spraytec instrument is used to measure the particle size distribution. The Dv50 is the term to describe the maximum particle size diameter below which 50% of the sample volume possesses, also known as the median particle size by volume. The Malvern Spraytec instrument uses the technique of laser diffraction for measurement of the size of the spray particles. The intensity of light scattered as a laser beam passes through a spray is measured. This data is then analysed to calculate the size of the particles that created the scattering pattern. A Malvern Spraytec 2000 is used according to the manufacturer's instructions. Test samples have a temperature between 20° C. to 22° C.

In at least one embodiment, the ejected composition comprises/consists of particles having an average particle size distribution (Dv50) of from about 35 micron, or from about 40 micron, or from about 45 micron, or from about 50 micron, or from about 55 micron, or from about 60 micron, to about 140 micron, or to about 120 micron, or to about 110 micron, or to about 100 micron, or to about 90 micron, or to about 85 micron, or to about 80 micron, or to about 75 micron, or to about 70 micron, or about to 65 micron.

Water

The hairstyling formulation comprises from about 30% to about 60% water, by total weight of the hairstyling formulation and propellant. The water is important since it provides a solvent for the hairstyling polymer and other ingredients in the hairstyling formulation. Water has the advantage that it is readily available, highly affordable, sustainable and environmentally friendly. For example, water is not a VOC. Furthermore, many useful ingredients for the hairstyling formulation dissolve in water i.e. are water soluble, which is another advantage. In at least one embodiment, the hairstyling formulation comprises from about 33%, or from about 34%, or from about 35%, or from about 36%, or from about 37%, or from about 36%, or from about 38%, or from about 39%, or from about 40%, or from about 41%, or from about 42%, or from about 43%, or from about 44%, or from about 45% to about 58% water, or to about 57%, or to about 56%, or to about 55%, or to about 54%, or to about 53%, or to about 52%, or to about 51%, or to about 50%, or to about 49%, or to about 48% water, by total weight of the hairstyling formulation and propellant.

Hairstyling Polymer

The hairstyling formulation comprises from about 5.0% to about 15% hairstyling polymer, by total weight of the hairstyling formulation and propellant. The amount of hairstyling polymer is important in balancing hold performance and on-hair wetness. The amount of hairstyling polymer drives the hold performance, but is limited by a maximum sprayable viscosity. In at least one embodiment, hairstyling formulation comprises from about 5.5%, or from about 6%, or from about 7%, or from about 8%, or from about 9% to about 14%, or to about 13%, or to about 12%, or to about 11%, or to about 10% hairstyling polymer, by total weight of the hairstyling formulation and propellant. These amounts may be the total amount of hairstyling polymer in the hairstyling formulation.

The preferred hairstyling polymer or mixture of hairstyling polymers are water-soluble hairstyling polymers that provide a viscosity of about 6 cSt or less as measured before the addition of propellant. This water-based hairstyling formulation of hairstyling polymer(s) is then pressurized in a container with a liquefied gas propellant. When the pressure is released, the liquid boils carrying with it the water and hairstyling polymer(s) plus any optional ingredients. Therefore a homogeneous mixture of the hairspray formulation and the liquefied gas propellant in the pressurized can is highly desired for a homogeneous ejected composition to be delivered to the hair when the product is sprayed. Homogeneity can happen immediately or over a period of time after the can is pressurized. This can also be achieved by shaking the can prior to spraying the product. For example, it is common in other aerosol products (such as mousses) for the propellant to be insoluble with the rest of the formulation in the can. The preferred hairstyling polymers and or mixture of hairstyling polymers of this invention are selected based on their ability to form a homogenous mixture when mixed with water and liquefied gas propellant in the pressurized can.

In at least one embodiment, the hairstyling polymer is selected from hairstyling polymers forming a homogeneous mixture with water and liquefied gas propellant. In at least one embodiment, the hairstyling polymer is selected from hairstyling polymers forming a homogeneous mixture with water and dimethyl ether. By "homogeneous mixture" herein means a mixture having a single phase, therefore components of the homogeneous mixture have the same proportions throughout the mixture.

The hairstyling polymer according to the present invention may be any water-soluble film-forming polymer or mixture of such polymers. This includes homopolymers or copolymers of natural or synthetic origin having functionality rendering the polymers water-soluble such as hydroxyl, amine, amide or carboxyl groups.

In at least one embodiment, the water-soluble hairstyling polymers when diluted in water at the range claimed, form transparent or semi-transparent stable solutions. Depending on the specific polymer type, it may be necessary to adjust the pH of the formulation or to neutralize the formulation after addition of the polymer to water to achieve water solubility. These methods are well-known in the water soluble polymer applications industry and are typically instructed with the supplied polymer sample. The hairstyling polymer may be classified into two types, (totally) synthetic polymers and natural products together with their chemically modified derivatives and further can be grouped into three main headings; naturally occurring, semi-synthetic and completely synthetic polymers. In at least one embodiment, the hairstyling polymer is selected from the group consisting of: cationic hairstyling polymers, anionic hairstyling polymers, nonionic hairstyling polymers, and amphoteric hairstyling polymers. The molecular weight of the hairstyling polymers should be such that the hairstyling formulation without propellant meets the viscosity requirement range specified. In at least one embodiment, the hairstyling polymers are linear or branched.

In at least one embodiment, the hairstyling polymer is a cationic hairstyling polymer or a mixture of cationic hairstyling polymers. In at least one embodiment, the cationic hairstyling polymer is selected from the group consisting of: quaternized acrylates or methacrylates; quaternary homopolymers or copolymers of vinylimidazole; homopolymers or copolymers comprising a quaternary dimethdiallyl ammonium chloride; non-cellulosic cationic polysaccharides; cationic cellulose derivatives; chitosans and derivatives thereof; and mixtures thereof.

In at least one embodiment, the cationic hairstyling polymer is selected from quaternized acrylates or methacrylates. In at least one embodiment, the cationic hairstyling polymer is a copolymer comprising: a) at least one of: quaternized dialkylaminoalkyl acrylamides (e.g. Quaternized dimethyl amino propyl methacrylamide); or quaternized dialkylaminoalkyl acrylates (e.g. quaternized dimethyl aminoethyl methacrylate) and b) one or more monomers selected from the group consisting of: vinyllactams such as vinylpyrrolidone or vinylcaprolactam; acrylamides, methacrylamides which may or may not be substituted on the nitrogen by lower alkyl groups (C1-C4) (e.g. N-tertbutylacrylamide); esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; and allyl esters or methallyl esters. The counter ion can be either a methosulfate anion or a halide such as chloride or bromide.

In at least one embodiment, the cationic hairstyling polymer is a quaternary homopolymer or copolymer of vinylimidazole. In at least one embodiment, the cationic hairstyling polymer is a copolymer comprising a) a quaternized vinylimizazole and b) one or more other monomers. The other monomer may be selected from the group consisting of: vinyllactams such as vinylpyrrolidone or vinylcaprolactam such as vinylpyrrolidone/quaternized vinylimidazole (PQ-16) such as that sold as Luviquat FC-550 by BASF; acrylamides, methacrylamides which may or may not be substituted on the nitrogen by lower alkyl groups (C1-C4) (e.g. N-tertbutylacrylamide); esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters. The counter ion can be either a methosulfate anion or a halide such as chloride or bromide.

In at least one embodiment, the cationic hairstyling polymer comprises a dimethdiallyl ammonium chloride. In at least one embodiment, the cationic hairstyling polymer is a homopolymer or copolymer comprising a quaternary dimethdiallyl ammonium chloride and another monomer. Such other monomer may be selected from the group consisting of: acrylamides, methacrylamides which may or may not be substituted on the nitrogen by lower alkyl groups (C1-C4) (e.g. N-tertbutylacrylamide); vinyllactams such as vinylpyrrolidone or vinylcaprolactam; esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters. The counter ion can be either a methosulfate anion or a halide such as chloride or bromide.

In at least one embodiment, the cationic hairstyling polymer is a non-cellulosic cationic polysaccharide. In at least one embodiment, the cationic hairstyling polymer is a guar gums such as those containing trialkylammonium cationic groups. For example, such as guar hydroxypropyltrimonium chloride, which is available as N-Hance 3269 from Ashland.

In at least one embodiment, the cationic hairstyling polymer is a cationic cellulose derivative. In at least one embodiment, the cationic hairstyling polymer is a copolymers of cellulose derivatives such as hydroxyalkylcelluloses (e.g. hydroxymethyl-, hydroxyethyl- or hydroxypropylcelluloses) grafted with a water-soluble monomer comprising a quaternary ammonium (e.g. glycidytrimethyl ammonium, methacryloyloxyethyltrimethylammonium, or a methacrylamidopropyltrimethylammonium, or dimethyldiallylammonium salt). For example, such as hydroxyethylcellulose dimethyldiallyammonium chloride [PQ4] sold as Celquat L200 by Akzo Nobel, or such as Quaternized hydroxyethylcellulose [PQ10] sold as UCARE JR125 by Dow Personal Care.

In at least one embodiment, the cationic hairstyling polymer is selected from chitosans and derivatives thereof. A derivative of a chitosan includes salts of chitosans. The salts can be chitosan acetate, lactate, glutamate, gluconate or pyrrolidinecarboxylate preferably with a degree of hydrolysis of at least 80%. A suitable chitosan includes Hydagen HCMF by Cognis.

In at least one embodiment, the hairstyling polymer is an anionic hairstyling polymer or a mixture of anionic hairstyling polymers. In at least one embodiment, the anionic hairstyling polymer is selected from those comprising groups derived from carboxylic or sulfonic acids. Copolymers containing acid units are generally used in their partially or totally neutralized form, more preferably totally neutralized. In at least one embodiment, the anionic hairstyling polymer comprises: (a) at least one monomer derived from a carboxylic acid such as acrylic acid, or methacrylic acid or crotonic acid or their salts, or C4-C8 monounsaturated polycarboxylic acids or anhydrides (e.g. maleic, furamic, itaconic acids and their anhydrides) and (b) one or more monomers selected from the group consisting of: esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); acrylamides, methacrylamides which may or may not be substituted on the nitrogen by lower alkyl groups (C1-C4); N-alkylated acrylamide (e.g. N-tertbutylacrylamide); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters; vinyllactams such as vinylpyrrolidone or vinylcaprolactam; alkyl maleimide, hydroxyalkyl maleimide (e.g. Ethyl/Ethanol Maleimide). When present the anhydride functions of these polymers can optionally be monoesterified or monoamidated. In at least one embodiment, the anionic hairstyling polymer comprises monomers derived from a sulfonic acid. In at least one embodiment, anionic polymers comprise: (a) at least one monomer derived from a sulfonic acid such as vinylsulfonic, styrenesulfonic, naphthalenesulfonic, acrylalkyl sulfonic, acrylamidoalkylsulfonic acid or their salts and (b) one or more monomers selected from the group consisting of: esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); acrylamides, methacrylamides which may or may not be substituted on the nitrogen by lower alkyl groups (C1-C4); N-alkylated acrylamide (e.g. N-tertbutylacrylamide); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters; vinyllactams such as vinylpyrrolidone or vinylcapro lactam; alkyl maleimide, hydroxyalkyl maleimide (e.g. Ethyl/Ethanol Maleimide). When present the anhydride functions of these polymers can optionally be monoesterified or monoamidated.

In at least one embodiment, the anionic hairstyling polymer is a water-soluble polyurethane.

In at least one embodiment, the anionic hairstyling polymers are advantageously selected from: copolymers derived from acrylic acid such as the acrylic acid/ethylacrylate/N-tert-butylacrylamide terpolymer such as that sold as Ultrahold 8 by BASF; Octylacrylamide/Acrylates/Butylaminoethyl/Methacrylate Copolymer such as that sold as Amphomer by Akzo Nobel; methacrylic acid/ester acrylate/ester methacrylate such as that sold as Balance CR by Akzo Nobel; Octylacrylamide/Acrylates/Butylaminoethyl Methacrylate Copolymer such as that sold as Balance 47 by Akzo Nobel; methacrylic acid/hydroxyethylmethacrylate/various acrylate esters such as that known as Acudyne 1000 sold by Dow Chemical; acrylates/hydroxyethylmethacrylate such as that sold as Acudyne 180 by Dow Chemical; methacrylic acid/hydroxyethylmethacrylate/various acrylate esters such as that sold as Acudyne DHR by Dow Chemical; n-butyl methacrylate/methacrylic acid/ethyl acrylate copolymer such as that sold as Tilamar Fix A-1000 by DSM; copolymers derived from crotonic acid, such as vinyl acetate/vinyl tertbutylbenzoate/crotonic acid terpolymers and the crotonic acid/vinyl acetate/vinyl neododecanoate terpolymers such as that sold as Resin 282930 by Akzo Nobel. Preferred hairstyling polymers derived from sulfonic acid include: sodium polystyrene sulfonate sold as Flexan 130 by Ashland; sulfopolyester (also known as Polyester-5) such as that sold as Eastman AQ 48 by Eastman; sulfopolyester (also known as Polyester-5) such as that sold as Eastman AQ S38 by Eastman; sulfopolyester (also known as Polyester-5) such as that sold as Eastman AQ 55 by Eastman. In at least one embodiment, the anionic hairstyling polymers are preferably selected from: copolymers derived from acrylic acid such as the acrylic acid/ethylacrylate/N-tert-butylacrylamide terpolymers (such as that sold as Ultrahold 8 by BASF); Octylacrylamide/Acrylates/Butylaminoethyl/Methacrylate Copolymer such as that sold as Amphomer; methacrylic acid/ester acrylate/ester methacrylate such as that sold as Balance CR by Akzo Nobel; Octylacrylamide/Acrylates/Butylaminoethyl Methacrylate Copolymer such as that sold as Balance 47 by Akzo Nobel; methacrylic acid/hydroxyethylmethacrylate/various acrylate esters such that known as Acudyne 1000 sold by Dow Chemical; acrylates/hydroxyethylmethacrylate such as that sold as Acudyne 180 by Dow Chemical; methacrylic acid/hydroxyethylmethacrylate/various acrylate esters such as that sold as Acudyne DHR by Dow Chemical; n-butyl methacrylate/methacrylic acid/ethyl acrylate copolymer such as that sold as Tilamar Fix A-1000 by DSM; copolymers derived from crotonic acid, such as vinyl acetate/vinyl tertbutylbenzoate/crotonic acid terpolymers and the crotonic acid/vinyl acetate/vinyl neododecanoate terpolymers such as that sold as Resin 282930 by Akzo Nobel. Preferred hairstyling polymers derived from styrene sulfonic acid include: sodium polystyrene sulfonate sold as Flexan 130 by Ashland; sulfopolyester (also known as Polyester-5) such as that sold as Eastman AQ 48 by Eastman; sulfopolyester (also known as Polyester-5) such as that sold as Eastman AQ S38 by Eastman; sulfopolyester (also known as Polyester-5) such as that sold as Eastman AQ 55 by Eastman.

In at least one embodiment, the hairstyling polymer is an anionic hairstyling polymer, and wherein the anionic hairstyling polymer is selected from: copolymers derived from acrylic acid such as the acrylic acid/ethylacrylate/N-tert-butylacrylamide terpolymers; Octylacrylamide/Acrylates/Butylaminoethyl/Methacrylate Copolymers; methacrylic acid/ester acrylate/ester methacrylates; Octylacrylamide/Acrylates/Butylaminoethyl Methacrylate Copolymer; methacrylic acid/hydroxyethylmethacrylate/various acrylate esters; acrylates/hydroxyethylmethacrylate; methacrylic acid/hydroxyethylmethacrylate/various acrylate esters; n-butyl methacrylate/methacrylic acid/ethyl acrylate copolymers; copolymers derived from crotonic acid, such as vinyl acetate/vinyl tertbutylbenzoate/crotonic acid terpolymers; and the crotonic acid/vinyl acetate/vinyl neododecanoate terpolymers; and mixtures thereof.

In at least one embodiment, the hairstyling polymer is a polyurethane dispersed in water. Such polyurethanes include those such as adipic acid, 1-6 hexandiol, neopentyl glycol, isophorone diisocyanate, isophorone diamine, N-(2-aminoethyl)-3-aminoethanesulphonic acid, sodium salt (also known as Polyurethane-48) such as that sold as Baycusan C1008 by Bayer; and such as isophorone diisocyanate, dimethylol propionic acid, 4,4-isopropylidenediphenol/propylene oxide/ethylene oxide (also known as Polyurethene-14) such as that sold as a mixture under the name of DynamX H20 by Akzo Nobel.

In at least one embodiment, the hairstyling polymer is a nonionic hairstyling polymer or a mixture of nonionic hairstyling polymers. Suitable synthetic non-ionic hairstyling polymers include: homopolymers and copolymers comprising: (a) at least one of the following main monomers: vinylpyrrolidone; vinyl esters grafted onto a polyalkylene glycol such as polyethylene glycol; acrylate esters grafted onto a polyalkylene glycol such as polyethylene glycol or acrylamide and (b) one or more other monomers such as vinyl esters (e.g. vinyl acetate or vinyl propionate, vinyl tert-butyl-benzoate); alkylacrylamine (e.g. tert-butylaminoethyl methacrylate, dimethyl aminoethyl methacrylate); vinylcaprolactam; hydroxyalkylated acrylamide; amino alkylated acrylamide (e.g. dimethyl amino propyl methacrylamide); vinyl ether; alkyl maleimide, hydroxyalkyl maleimide (e.g. Ethyl/Ethanol Maleimide).

In at least one embodiment, the non-ionic hairstyling polymer is preferably selected from vinylpyrrolidone/vinyl acetate copolymers (such as that sold as LUVISKOL VA 64 by BASF and such as vinylpyrrolidone homopolymer such as that sold as PVPK30 by Ashland).

In at least one embodiment, the non-ionic hairstyling polymer is a water-soluble natural polymer being a cellulose derivative, such as hydroxyalkylcelluloses (e.g. hydroxymethyl-, hydroxyethyl- or hydroxypropylcelluloses) and starches.

In at least one embodiment, the hairstyling polymer is an amphoteric hairstyling polymer or a mixture of amphoteric hairstyling polymers. Suitable synthetic amphoteric hairstyling polymers include those comprising: an acid and a base like monomer; a carboxybetaine or sulfobetaine zwitterionic monomer; and an alkylamine oxide acrylate monomer. In at least one embodiment, the amphoteric comprising: (a) at least one monomer containing a basic nitrogen atom such as a quaternized dialkylaminoalkyl acrylamide (e.g. Quaternized dimethyl amino propyl methacrylamide) or a quaternized dialkylaminoalkyl acrylate (e.g. quaternized dimethyl aminoethyl methacrylate) and (b) at least one acid monomer comprising one or more carboxylic or sulfonic groups such as acrylic acid, or methacrylic acid or crotonic acid or their salts, or C4-C8 monounsaturated polycarboxylic acids or anhydrides (e.g. maleic, furamic, itaconic acids and their anhydrides) and (c) one or more monomers selected from acrylamides, methacrylamides which may or may not be substituted on the nitrogen by lower alkyl groups (C1-C4) (e.g. N-tertbutylacrylamide); vinyllactams such as vinylpyrrolidone or vinylcapro lactam; esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters. In an embodiment, the amphoteric hairstyling polymer comprises at least one carboxybetaine or sulfobetaine zwitterionic monomer such as carboxybetaine methacrylate and sulfobetaine methacrylate. In at least one embodiment, the amphoteric hairstyling polymer comprises: (a) at least one carboxybetaine or sulfobetaine zwitterionic monomer such as carboxybetaine methacrylate and sulfobetaine methacrylate; and (b) a monomer selected from the group consisting of: acrylamides, methacrylamides which may or may not be substituted on the nitrogen by lower alkyl groups (C1-C4) (e.g. N-tertbutylacrylamide); vinyllactams such as vinylpyrrolidone or vinylcapro lactam; esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters. In at least one embodiment, the amphoteric hairstyling polymer comprises at least an alkylamine oxide acrylate. In at least one embodiment, the amphoteric hairstyling polymer comprises: (a) an ethylamine oxide methacrylate; and (b) a monomer selected from the group consisting of: acrylamides, methacrylamides which may or may not be substituted on the nitrogen by lower alkyl groups (C1-C4) (e.g. N-tertbutylacrylamide); vinyllactams such as vinylpyrrolidone or vinylcapro lactam; esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); hydroxyalkylated acrylamide; amino alkylated acrylamide (e.g. dimethyl amino propyl methacrylamide); alkylacrylamine (e.g. tert-butylaminoethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters. An example of such an amphoteric hairstyling polymer is acrylates/ethylamine oxide methacrylate sold as Diaformer Z 731 N by Clariant.

In at least one embodiment, the hairstyling polymer is selected from the group consisting of: acrylates copolymers of two or more monomers of (meth)acrylic acid or one of their simple esters; octylacrylamide/acrylate/butylaminoethyl methacrylate copolymers; acrylates/hydroxyesters acrylates copolymers of butyl acrylate, methyl methacrylate, methacrylic acid, ethyl acrylate and hydroxyethyl methacrylate; polyurethane-14/AMP-acrylates copolymer blend; and mixtures thereof.

In at least one embodiment, the hairstyling formulation is substantially free of water-insoluble polymers, in particular, water-insoluble hairstyling polymers. Polymers that are not miscible in water should be avoided for the present invention. Polymers of high molecular weight (>200,000 g/mol) should be avoided or only used at very low levels such that the hairstyling formulation does not exceed the viscosity requirements. In at least one embodiment, the hairstyling formulation is substantially free of a polymer having a molecular weight of greater than 200,000 g/mol. In at least one embodiment, the hairstyling formulation is substantially free of a polymer comprising at least two long hydrophobic (e.g. linear fatty chains of 10 carbons or more) grafts. Such polymers with such grafts can lead to associative interactions in the hairstyling formulation which can drive viscosity up without contributing to the strength of the film delivered to the hair.

Optional Ingredients

In at least one embodiment, the hairstyling formulation comprises a panthenol compound and/or a silicone compound. In at least one embodiment, the panthenol compound is selected from the group consisting of: panthenol, a pantothenic acid derivative, and mixtures thereof. In at least one embodiment, the panthenol compound is selected from the group consisting of: D-panthenol ([R]-2,4-dihydroxy-N-[3-15-(hydroxypropyl)]-3,3-dimethylbutamide), D/L-panthenol, pantothenic acids and their salts, panthenyl triacetate, royal jelly, panthetine, pantotheine, panthenyl ethyl ether, pangamic acid, pantoyl lactose, Vitamin B complex, and mixtures thereof. The panthenol compound is useful in view of providing excellent hair look and feel benefits. The hairstyling formulation may comprise from about 0.1% to about 0.6%, or from about 0.1% to about 0.3%, of a panthenol compound, by total weight of the hairstyling formulation and the propellant. In at least one embodiment, the hairstyling formulation comprises a silicone compound. The silicone is useful because it gives a smoother feel and also shine to the hair. In at least one embodiment, the silicone compound is a dimethicone compound. In at least one embodiment, the silicone compound is a PEG dimethicone, for example PEG-12 dimethicone.

The hairstyling formulation may further comprise a surfactant. The hairstyling formulation may comprise 1% or less surfactant, or 0.6% or less, or 0.4% or less, or 0.3% or less, by total weight of the hairstyling formulation and propellant. In at least one embodiment, the surfactant is selected from the group consisting of cationic surfactants, non-ionic surfactants, anionic surfactants, and mixtures thereof. Cationic surfactants may be selected from the group consisting of cetrimonium chloride (e.g. Quartamin 60L-G from Kao; DEHYQUART A-CA/DETEX; ARQUAD 16-25 LO); cocamidopropyl hydroxysultaine (e.g. REWOTERIC AM CAS); cocamidopropyl betaine (e.g. TEGO BETAIN F 50); betaine; and mixtures thereof. Non-ionic surfactants may be selected from the group consisting of: castor oil PEG-40 H (e.g. NEODOL10 91-8); laureth-4 (e.g. DEHYDOL LS 4 DEO N); laureth-9; decyl glucoside (e.g. Plantacare 2000); polysorbate 20 (e.g. TWEEN 20 PHARMA from UNIQEMA); PEG-25 hydrogenated castor oil (e.g. SIMULSOL 1292 DF from SEPPIC); PEG-40 hydrogenated castor oil (e.g. CREMOPHOR CO 410 from BASF); PPG-1-PEG-9-laurylglycolether (e.g. Eumulgin L); siloxane polyalkyleneoxide copolymer (Silwet® L7604 from Momentive); and polydimethylsiloxane methylethoxylate (Silwet® L7600 from Momentive); and mixtures thereof. A suitable anionic surfactant is dioctyl sodium sulfosuccinate (DOSS or 1,4-dioctoxy-1,4-dioxobutane-2-sulfonic acid), an example of which is Aerosol OT-70 PG from Cytec. In at least one embodiment, the surfactant is selected from the group consisting of: castor oil PEG-40 H; cetrimonium chloride; laureth-4; laureth-9; decyl glucoside; cocamidopropyl hydroxysultaine; polysorbate 20; siloxane polyalkyleneoxide copolymer; dioctyl sodium sulfosuccinate; and mixtures thereof In at least one embodiment, the hairstyling formulation comprises a neutraliser. Suitable neutralisers include potassium hydroxide, sodium hydroxide, triisopropanolamine (TIPA), 2-aminobutanol, 2-aminomethyl propanol (AMP), aminoethylpropandiol, dimethyl stearamine (Armeen 18 D), sodium silicate, tetrahydroxypropyl ethylenediamine (Neutrol® TE), ammonia (NH3), triethanolamine, trimethylamine (Tris AminoUltra), aminomethylpropandiol (AMPD). In at least one embodiment, the neutralising agent is 2-aminobutanol, ammonia, or 2-aminomethyl propanol.

The hairstyling formulation may comprise at least one preservative. The preservative may be present in an amount of less than about 1.5%, or 0% to 1%, or 0.01% to 1%, by total weight of the hairstyling formulation and propellant. Suitable preservatives include: phenoxyethanol (e.g. Euxyl® PE 9010), benzyl alcohol, propylene glycol, PHMB (Poly-aminopropyl biguanide), Optiphen (Phenoxyethanol+ caprylyl glycol) from ISP, Symtriol (1,2-octanediol and 1,2 hexanediol, methylbenzyl alcohol) from Symrise, octylsalicylate, 1,3-bis(hydroxymethyl)-5,5-dimethylimidazolidine-2,4-dione (DMDM hydantoin; Nipaguard® DMDMH by Clariant), EDTA (Rexat), butylene glycol (Dekaben LMB), and parben types e.g. methylparaben (e.g. PHB methyl ester from Schütz & Co., or SLI Chemicals, or Nipagin® M), propylparaben (PHB-propylester from Solvadis Specialties).

The hairstyling formulation may further comprise at least one perfume or fragrance. The hairstyling formulation may comprise a maximum of about 0.5% perfume or fragrance, or from about 0% to about 0.4%, or from about 0.03% to about 0.3%, by total weight of the hairstyling formulation and propellant.

In at least one embodiment, the hairstyling formulation comprises a corrosion inhibitor. In at least one embodiment, the corrosion inhibitor is EDTA.

The hairstyling formulation may further comprise vitamins and amino acids such as: water-soluble vitamins such as vitamin B1, B2, B6, B12, C, pantothenic acid, pantothenyl ethyl ether, panthenol, biotin, and their derivatives, water soluble amino acids such as asparagine, alanine, indole, glutamic acid and their salts, water insoluble vitamins such as vitamin A, D, E, and their salts and/or derivatives, water insoluble amino acids such as tyrosine, tryptamine, viscosity modifiers, dyes, non-volatile solvents or diluents (water soluble and insoluble), pearlescent aids, foam boosters, additional surfactants or non-ionic cosurfactants, pediculocides, pH adjusting agents, perfumes, preservatives, chelants, proteins, skin active agents, sunscreens, UV absorbers, vitamins, niacinamide, caffeine and minoxidil. The hairstyling formulation may comprise from about 0.01% to about 5% vitamins and/or amino acids, by total weight of the hairstyling formulation and propellant. The hairstyling formulation may further comprise pigment materials such as inorganic pigments, nitroso-, monoazo-, disazo- compounds, carotenoid, triphenyl methane, triaryl methane, chemicals of the quinoline, oxazine, azine, or anthraquinone type, as well as compounds which are indigoid, thionindigoid, quinacridone, phthalocyanine, botanical, natural colors, and water-soluble components. The hairstyling formulation may comprise from about 0.0001% to about 5% pigment materials, by total weight of the hairstyling formulation and propellant. The hairstyling formulation may also contain antimicrobial agents which are useful as cosmetic biocides. The hairstyling formulation may comprise from about 0.01% to about 5% antimicrobial agents, by total weight of the hairstyling formulation and propellant.

Propellant

The product comprises a liquefied gas propellant. The liquefied gas propellant may be selected from the group consisting of dimethylether (DME), 1,1-difluoroethane (HFC-152a), 1,1,1,2-tetrafluoroethane (HFC-134a), pentane, n-butane, iso-butane, propane, trans-1,3,3,3-tetrafluoropropene (HFO-1234ze), and mixtures thereof. In at least one embodiment, the liquefied gas propellant is dimethylether (DME) or 1,1-difluoroethane (HFC-152a). In at least one embodiment, the liquefied gas propellant is dimethylether. Dimethyl ether is useful in the invention in view of it forming a homogenous solution with the hairstyling formulation.

In at least one embodiment, the product comprises from about 35% to about 50% liquefied gas propellant, or from about 40% to about 45% liquefied gas propellant, by total weight of the hairstyling formulation and propellant. In at least one embodiment, the product comprises from about 35% to about 50% dimethylether, or from about 40% to about 45% dimethylether, by total weight of the hairstyling formulation and propellant.

In at least one embodiment, the liquefied gas propellant and hairstyling formulation freely communicate with one another inside the reservoir. In at least one embodiment, the liquefied gas propellant and hairstyling formulation are not stored in separate compartments.

The product comprises a pressurisable container. The pressure inside the reservoir can be measured with a pressure gauge (GCAS #60001439). In at least one embodiment, the pressure inside the container is from about 1 bar to about 7 bar, or from about 1.5 bar to about 5 bar, measured at 20° C. In at least one embodiment where the propellant is iso-butane, propane, or dimethylether the pressure inside the container is from about 3 bar to about 4 bar, at 20° C. When the propellant is n-butane, the pressure inside the container may be from about 1.5 bar to about 2 bar, or from about 1.7 bar to about 1.9 bar, measured at 20° C.

In at least one embodiment, the product comprises about 50% or less volatile organic compound (VOC). VOCs can cause health and environmental concerns. This is particularly relevant for manufacturing and in that certain countries have restrictions on the amount of VOC that can be used in household products. Indeed, it is usual to market different hairspray formulations in Europe versus in North America, for example, in view of the different regulatory requirements. Therefore, hairsprays having reduced VOCs are useful in view of providing a globally-marketable hairspray product. As used herein, the US regulatory law vis-à-vis the definition of a VOC applies herein. The definition of VOC for US legislative purposes (U.S. EPA 40 CFR 51. 100[s]) defines only those organic compounds without negligible photochemical reactivity.

Spraying Device

The product comprises a spraying device attached to the container 118 for dispensing the hairstyling formulation from the reservoir 204 of the container 118, wherein the spraying device comprises a valve 205 and a nozzle, wherein the valve comprises a valve body 113, a stem 107 and a spring means 108, and wherein the valve body 113 houses an insert 109, and wherein the insert 109 comprises an insert orifice 109a and at least two channels 110a, 110b, wherein the channels 110a, 110b are tangentially disposed about the insert orifice 109a, and wherein the valve body 113 comprises at least two vapour taps 211a, 211b, and wherein the insert orifice 109a is capable of being in liquid communication with the hairstyling formulation in the reservoir 204.

The features of the insert 109 permit a large amount of headspace propellant gas to enter the flowstream of the hairstyling formulation in the valve 205. This headspace propellant gas is injected into the hairstyling flowstream in the valve body 113 via the insert 109 which due to at least two vapour taps 211a, 211b and the channels 110a, 110b imparts a swirling motion to the propellant gas at it enters the hairspray formulation flowstream. The volume of propellant gas combined with the imparted propellant gas circular motion is much more efficient at breaking the product flow into particles; thereby resulting in improved i.e. reduced particle size distribution for the resulting ejected composition.

In at least one embodiment, the valve body 113 comprises a valve tailpiece 115, and wherein the valve tailpiece 115 has an orifice, which receives a dip tube 116. In at least one embodiment, the channels 110a; 110b are on the bottom of the insert 110. In at least one embodiment, the insert orifice 109a is capable of being in liquid communication with the hairstyling formulation in the reservoir 204 via a dip tube 116 connected to a valve tailpiece 115. In at least one embodiment, the vapour taps 211a, 211b converge on the channels 110a, 110b. In at least one embodiment, the channels 110a, 110b converge on the insert orifice 109a. In at least one embodiment, the valve body 113 is free of a vapour tap not converging on a channel 110. Such a vapour tap that does not converge with the channel 110 is depicted, for exemplification, as reference sign 113a in FIG. 1. Such a vapour tap, or vapour housing hole, as it is sometimes referred to in the literature, is not useful herein. Indeed, this type of vapour tap does not introduce sufficient quantity of propellant gas or provide efficient insertion into the flowstream for sufficient particle size breakup. If used in combination with the features of the present valve 205 it would deflect propellant gas flowing through the at least two vapour taps 211a, 211b and the at least two channels 110a, 110b. Thus, the swirling effect would be reduced.

In at least one embodiment, the vapour taps 211a, 211b have orifice dimensions of from about 0.22 mm to about 0.28 mm×from about 0.30 mm to about 0.36 mm, or of from about 0.24 mm to about 0.26 mm×from about 0.32 mm to about 0.34 mm.

In at least one embodiment, the channels 110a; 110b on the bottom of the insert 110 abut an internal flat base of the valve body 113 to create two internal gas metering slots that are in gaseous communication with the vapour taps 211a, 211b in the valve body 113, thereby creating a metered gas path from the headspace of the container to the inside of the valve body 113.

In at least one embodiment, the valve body (113) comprises a valve tailpiece (115), and wherein the valve tailpiece (115) has an orifice, which receives a dip tube (116); and wherein the dip tube (116) has an inner diameter, wherein the inner diameter is from about 0.030 inch (0.762 mm) to about 0.070 inch (1.778 mm), or from about 0.035 inch (0.889 mm) to about 0.065 inch (1.651 mm), or from about 0.040 inch (1.016 mm) to about 0.060 inch (1.524 mm), or from about 0.045 inch (1.143 mm) to about 0.055 inch (1.397 mm), or from about 0.035 inch (0.889 mm) to about 0.045 inch (1.143 mm) In at least one embodiment, the dip tube 116 has an inner diameter, wherein the inner diameter is from about 0.030 inch (0.762 mm) to about 0.070 inch (1.778 mm), or from about 0.035 inch (0.889 mm) to about 0.065 inch (1.651 mm), or from about 0.040 inch (1.016 mm) to about 0.060 inch (1.524 mm), or from about 0.045 inch (1.143 mm) to about 0.055 inch (1.397 mm), or from about 0.035 inch (0.889 mm) to about 0.045 inch (1.143 mm).

In at least one embodiment, the valve tailpiece 115 orifice (which receives the dip tube 116) has an inner diameter, wherein the inner diameter is from about 0.030 inch (0.762 mm) to about 0.070 inch (1.778 mm), or from about 0.035 inch (0.889 mm) to about 0.065 inch (1.651 mm), or from about 0.040 inch (1.016 mm) to about 0.060 inch (1.524 mm), or from about 0.045 inch (1.143 mm) to about 0.055 inch (1.397 mm), or from about 0.035 inch (0.889 mm) to about 0.045 inch (1.143 mm) In at least one embodiment, the insert orifice (109a) is capable of being in liquid communication with the hairstyling formulation in the reservoir (204) via a dip tube (116) connected to a valve tailpiece (115); and wherein the valve tailpiece (115) orifice has an inner diameter, wherein the inner diameter is from about 0.030 inch (0.762 mm) to about 0.070 inch (1.778 mm), or from about 0.035 inch (0.889 mm) to about 0.065 inch (1.651 mm), or from about 0.040 inch (1.016 mm) to about 0.060 inch (1.524 mm), or from about 0.045 inch (1.143 mm) to about 0.055 inch (1.397 mm), or from about 0.035 inch (0.889 mm) to about 0.045 inch (1.143 mm).

In at least one embodiment, the insert orifice 109a has a diameter of from about 0.020 inch (0.500 mm) to about 0.070 inch (1.778 mm) In at least one embodiment, the insert orifice 109a has a diameter of from about 0.030 inch (0.762 mm) to about 0.070 inch (1.778 mm), or from about 0.035 inch (0.889 mm) to about 0.065 inch (1.651 mm), or from about 0.040 inch (1.016 mm) to about 0.060 inch (1.524 mm), or from about 0.045 inch (1.143 mm) to about 0.055 inch (1.397 mm), or from about 0.035 inch (0.889 mm) to about 0.045 inch (1.143 mm) In at least one embodiment, the insert orifice 109a has a diameter of at least about 0.030 inch (0.762 mm).

In at least one embodiment, the channels 110a, 110b independently have a cross-section having a largest diameter of from about 0.005 inch (0.127 mm) to about 0.025 inch (0.635 mm), or from about 0.008 inch (0.203 mm) to about 0.020 inch (0.508 mm), or from about 0.010 inch (0.254 mm) to about 0.015 inch (0.381 mm), or from about 0.015 inch (0.381 mm) to about 0.018 inch (0.457 mm) In at least one embodiment, the channels 110a, 110b have dimensions (width×height) of from about 0.22 mm to about 0.28 mm×from about 0.30 mm to about 0.36 mm, or of from about 0.24 mm to about 0.26 mm×from about 0.32 mm to about 0.34 mm.

In at least one embodiment, the stem 107 has a stem orifice 105, which acts as an outlet for the contents of the container. In at least one embodiment, the stem orifice 105 has an inner diameter, wherein the inner diameter is from about 0.005 inch (0.127 mm) to about 0.025 inch (0.635 mm), or from about 0.008 inch (0.203 mm) to about 0.013 inch (0.340 mm), or from about 0.011 inch (0.279 mm) to about 0.014 inch (0.356 mm) In an embodiment, the stem orifice 105 has an inner diameter, wherein the inner diameter is from about 0.010 inch (0.254 mm) to about 0.020 inch (0.508 mm), or from about 0.015 inch (0.381 mm) to about 0.018 inch (0.457 mm).

In at least one embodiment, the spring means 108 is a spring 108. In at least one embodiment, the valve body 113 comprises castellations 112.

In at least one embodiment, the valve 205 further comprises a stem gasket 104 that seals against the seat for the stem gasket 106 on the stem 107 and thereby covers a side hole in the stem that leads to the stem orifice 105.

In at least one embodiment, the valve body 113, stem 107 and insert 109 are made of polyphenylene sulfone.

Figure 2B:
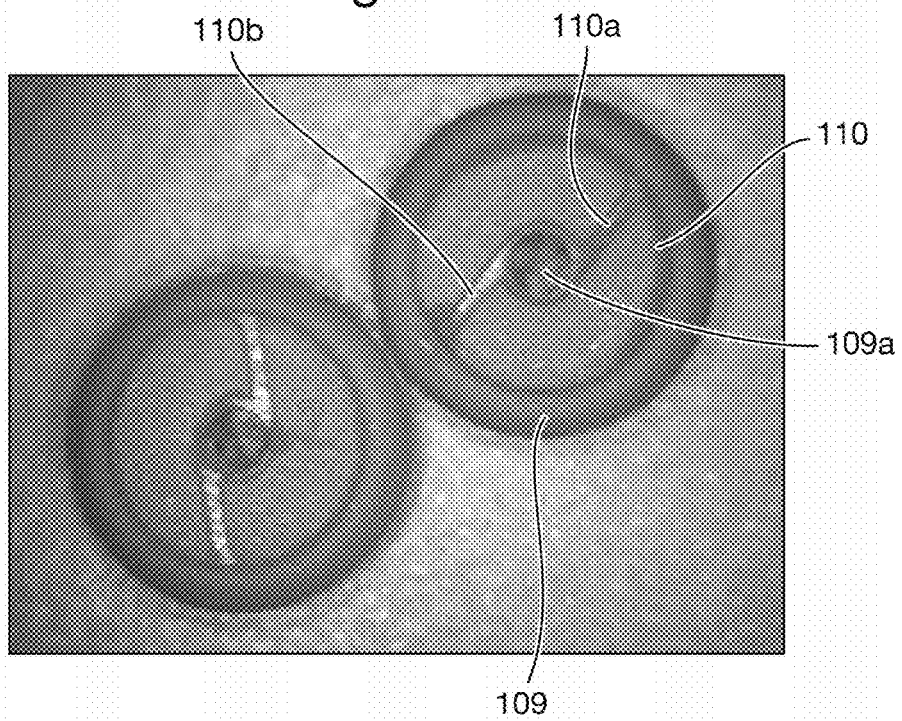
FIG. 2B: shows two inserts side-by-side.
Figure 4:
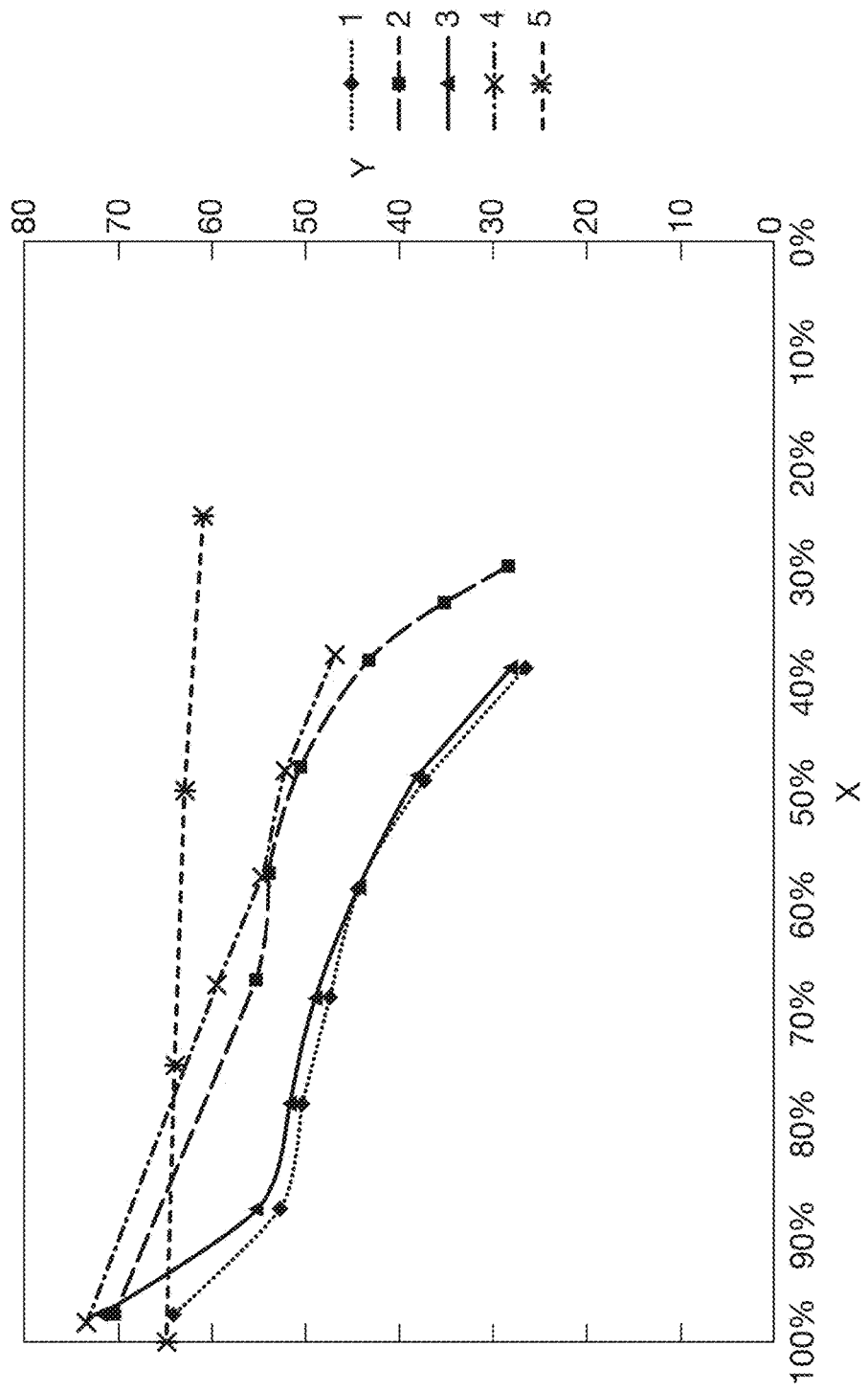
FIG. 4: is an analysis of Shernov and shows the relationship of pressure (axis Y, in psig) versus percentage of can contents remaining (axis X, %). Five different graphs are shown: 1-4 and 5. In can 1, the product contains 34% DME (propellant) and 7.2% hairstyling formulation. In can 2, the product contains 40% DME and 7.2% hairstyling formulation. In can 3, the product contains 34% DME (propellant) and 6.15% hairstyling formulation. In can 4, the product contains 40% DME (propellant) and 6.15% hairstyling formulation. Can 5 is a graph created according to the Table at the foot of column 5 as disclosed in Shernov.

A valve suitable for use in the present invention is an Ecosol™ device provided by Precision Valve, Peterborough, UK. Such a valve is disclosed in US2009/0124961A1, which is incorporated herein by reference. In particular, paragraphs [0053] to [0068] of US2009/0124961A1, as well as FIGS. 1 to 2 therein, are incorporated herein by reference.

Nozzles suitable for use in the present invention are available from Kosmos, Seaquist and Precision Valve. In at least one embodiment, the spraying device comprises a variable spray-angle nozzle, variable resin flux nozzle, tapered flow nozzle and/or helix atomizer nozzle. Such nozzles are disclosed in EP2570110A2, EP2570192A1, EP2570191A1, which are incorporated herein by reference. In particular, tapered flow nozzles and helix atomizer nozzles are disclosed in EP2570191A1 from paragraph 119 to 176, which refer to FIGS. 1-27 therein, are incorporated herein by reference.

DETAILED DESCRIPTION OF THE FIGURES

The stem gasket 104 is pre-assembled onto the stem 107 so that it seals against the seat for the stem gasket 106 on the stem 107 and covers a small side hole in the stem that leads to the stem orifice 105, which acts as an outlet for the contents of the container. A stainless steel spring 108 is then prefitted to the base of the stem moulding. The insert 109 is pre-assembled into the valve body 113 and sealingly seats the channels see FIG. 2: 110a; 110b formed on the bottom of the insert 110 against the internal flat base of the valve body 113 to create two internal gas metering slots that are in communication with the external slots 114 on the valve body 113, thereby creating a metered gas path from the headspace of the container to the inside of the valve body 113 when the valve is later clinched onto the container 118. The mounting cup 102 is prefitted with a cup gasket 103 to form a gas-tight seal against the container curl 117 when the assembled valve is clinched to the container by standard industry means. The subassemblies described above are then crimped together using a standard pedestal crimping tool to make the fully assembled valve 205. The stem gasket 104 is compressed by 50% in thickness by the crimping procedure, and the pedestal of the mounting cup 102 is deformed during crimping to engage and retain on the castellations 112 on the external surface of the valve body 113. A polyethylene dip tube 116 is push-fitted into sealing engagement with the tailpiece of the valve body 115 to complete the valve assembly. The container 118 is part-filled with hairstyling formulation inside the container 118 and with the liquefied gas propellant before the valve 205 and dip tube 116 are clinched onto the container curl 117 by use of conventional clinching equipment to make a gas-tight seal between the valve 205 and the container 118. The container 118 is then pressurized to the desired working pressure by gassing through the stem orifice 105. A fluid metering hole (not shown at the top of the tailpiece of the valve body 115 meters the hairstyling formulation into the valve body 113 from the bottom of the container 118 via the dip tube 116 and mixes the hairstyling formulation with the propellant entering the valve body 113 through the channels (see FIG. 2: 110a; 110b) on the base of the insert 110. When the stem 107 is depressed by more than approximately 1 mm through application of external force, the stem gasket 104 deforms away from the side hole in the stem gasket seat 106 area, opening a path between the container 118 and the external environment. When this external force is released, the spring 108 returns the stem to its fully closed position.

A standard 1 inch diameter aerosol valve 205 is clinched on to the top of the container 118 after filling with the hairspray formulation. The stem orifice 105 is the outlet of the stem 107. The container 118 comprises a container wall 201 and a reservoir 204 for storing a hairstyling formulation and a liquefied gas propellant. Activation of the valve 205 is achieved by through application of external force to depress the engaged stem 107 and thereby releasing the hairstyling formulation and propellant into the external environment via a nozzle (not shown), which is sized to engage with the valve 205. The valve 205 comprises a housing 207 which mounts the dip tube 116 and includes vapour taps 211a, 211b which admit propellant gas from reservoir 204 into the flow of hairstyling formulation which rises up the dip tube 116 on operation of valve 205 opening. The vapour taps 211a, 211b have a cross-sectional area such that the sum total ratio of this to the cross-sectional area of the fluid metering hole (not shown) at the top of the tailpiece of the valve body 115 (at the top of the dip tube) may be controlled to provide the desired propellant/hairstyling formulation ratio.

Exemplified Embodiments of the First Aspect

At least one embodiment relates to an aerosol hairspray product wherein the product comprises:

i. a pressurisable container 118 comprising a container wall 201 which encloses a reservoir 204 for storing a hairstyling formulation and a liquefied gas propellant;
ii. the hairstyling formulation comprising:
   (a) from about 30% to about 60% water, by total weight of the hairstyling formulation and propellant; and
   (b) from about 5.0% to about 15% hairstyling polymer by total weight of the hairstyling formulation and propellant, wherein the hairstyling polymer is water-soluble; and
   (c) less than 0.5% alcohol, by total weight of the hairstyling formulation and propellant, preferably substantially free of alcohol;
   and wherein the hairstyling formulation without propellant has a kinematic viscosity of from about 1.8 cSt to about 5.5 cSt, wherein the viscosity is measured at 20° C.+/−0.1° C.;
iii. a spraying device attached to the container 118 for dispensing the hairstyling formulation from the reservoir 204 of the container 118, wherein the spraying device comprises a valve 205 and a nozzle, wherein the valve comprises a valve body 113, a stem 107 and a spring means 108, and wherein the valve body 113 houses an insert 109, and wherein the insert comprises an insert orifice 109a and at least two channels 110a, 110b, wherein the channels 110a, 110b are tangentially disposed about the insert orifice 109a, and wherein the valve body 113 comprises at least two vapour taps 211a, 211b, and wherein the insert orifice 109a is capable of being in liquid communication with the hairstyling formulation in the reservoir 204; and wherein pressure inside the container is from about 3 bar to about 5 bar, at 20° C., or from about 3 bar to about 4 bar, at 20° C.

At least one embodiment relates to an aerosol hairspray product wherein the product comprises:
i. a pressurisable container 118 comprising a container wall 201 which encloses a reservoir 204 for storing a hairstyling formulation and a liquefied gas propellant;
ii. the hairstyling formulation comprising:
   (a) from about 30% to about 60% water, by total weight of the hairstyling formulation and propellant; and
   (b) from about 7.0% to about 14% hairstyling polymer by total weight of the hairstyling formulation and propellant, wherein the hairstyling polymer is water-soluble; and
   (c) less than 0.5% alcohol, by total weight of the hairstyling formulation and propellant, preferably substantially free of alcohol;
   and wherein the hairstyling formulation without propellant has a kinematic viscosity of from about 1.8 cSt to about 5.5 cSt, wherein the viscosity is measured at 20° C.+/−0.1° C.;
   and wherein the hairstyling formulation comprises an anionic hairstyling polymer;
iii. a spraying device attached to the container 118 for dispensing the hairstyling formulation from the reservoir 204 of the container 118, wherein the spraying device comprises a valve 205 and a nozzle, wherein the valve comprises a valve body 113, a stem 107 and a spring means 108, and wherein the valve body 113 houses an insert 109, and wherein the insert comprises an insert orifice 109a and at least two channels 110a, 110b, wherein the channels 110a, 110b are tangentially disposed about the insert orifice 109a, and wherein the valve body 113 comprises at least two vapour taps 211a, 211b, and wherein the insert orifice 109a is capable of being in liquid communication with the hairstyling formulation in the reservoir 204;
wherein the valve body 113 comprises a valve tailpiece 115, and wherein the valve tailpiece 115 has an orifice, which receives a dip tube 116; and wherein the dip tube 116 has an inner diameter, wherein the inner diameter is from about 0.035 inch (0.889 mm) to about 0.055 inch (1.397 mm);
wherein the stem 107 has a stem orifice 105, which acts as an outlet for the contents of the container; and wherein the stem orifice 105 has an inner diameter, wherein the inner diameter is from about 0.008 inch (0.203 mm) to about 0.014 inch (0.356 mm);
wherein the insert orifice 109a is capable of being in liquid communication with the hairstyling formulation in the reservoir 204 via a dip tube 116 connected to a valve tailpiece 115; and wherein the valve tailpiece 115 orifice has an inner diameter, wherein the inner diameter is from 0.035 inch (0.889 mm) to 0.055 inch (1.397 mm)

$2^{nd}$ Aspect

The second aspect relates to the use of the product according to the first aspect for styling hair. The descriptions vis-à-vis the aspects described above apply to and are suitable mutatis mutandis for this aspect as well.

$3^{rd}$ Aspect

The third aspect relates to a method of styling hair comprising:
i. providing the product according to the first aspect; and
ii. causing the product to spray at a delivery rate, wherein the delivery rate is from about 0.25 g/sec to about 0.45 g/sec; and wherein an ejected composition is sprayed, wherein the ejected composition comprises particles having an average particle size distribution (Dv50) of at least about 35 micron.

In at least one embodiment, the ejected composition comprises particles having an average particle size distribution (Dv50) of from about 35 micron, or from about 40 micron, or from about 45 micron, or from about 50 micron, or from about 55 micron, or from about 60 micron, to about 140 micron, or to about 120 micron, or to about 110 micron, or to about 100 micron, or to about 90 micron, or to about 85 micron, or to about 80 micron, or to about 75 micron, or to about 70 micron, or about to 65 micron. In at least one embodiment, the ejected composition comprises particles having an average particle size distribution (Dv50) of from about 40 micron to about 100 micron. Such average particle size distribution of from 40 micron to 100 micron is useful for providing optimal drying time on hair since the particles of ejected composition are well spread across the head of hair and yet a sufficient amount of hairstyling polymer is present in each particle (droplet) to provide sufficient hold (spot weld of hair fibres).

In at least one embodiment, said average particle size distribution is maintained over the lifetime of the product. "Lifetime of the product" as used herein, means from a full product until an insufficient amount of hairstyling formulation is present in the reservoir to be sprayed, for example substantially no hairstyling formulation is present in the reservoir. Maintenance of such average particle size distribution over the lifetime of the product is an advantage to the consumer who can thus expect excellent performance of the product until the product is 'empty'. Such benefit is, in particular, linked to the structural features of the valve—particularly in relation to: the insert 109 comprises an insert orifice 109a and at least two channels 110a, 110b, wherein the channels 110a, 110b are tangentially disposed about the insert orifice 109a, and wherein the valve body 113 comprises at least two vapour taps 211.

In at least one embodiment, the delivery rate is from about 0.26 g/sec, or from about 0.27 g/sec, or from about 0.28 g/sec, or from about 0.29 g/sec, or from about 0.30 g/sec, or from about 0.31 g/sec, or from about 0.32 g/sec, or from about 0.33 g/sec, or from about 0.34 g/sec, or from about 0.35 g/sec, or from about 0.36 g/sec, or from about 0.37 g/sec, or from about 0.38 g/sec, or from about 0.39 g/sec, or from about 0.40 g/sec to about 0.44 g/sec, or to about 0.43 g/sec, to about 0.42 g/sec, to about 0.41 g/sec, or to about 0.40 g/sec, or to about 0.39 g/sec, or to about 0.38 g/sec. In at least one embodiment, the delivery rate is from about 0.28 g/sec to about 0.45 g/sec. In at least one embodiment, the delivery rate is from about 0.36 g/sec to about 0.44 g/sec.

The descriptions vis-à-vis the aspects described above apply to and are suitable mutatis mutandis for this aspect as well.

Exemplified Embodiment of the 3$^{rd}$ Aspect

At least one embodiment relates to a method of styling hair comprising:
i. providing the product according to the first aspect; and
ii. causing the product to spray at a delivery rate, wherein the delivery rate is from about 0.28 g/sec to about 0.45 g/sec; and wherein an ejected composition is sprayed, wherein the ejected composition consists of particles having an average particle size distribution (Dv50) of from 40 micron to 100 micron, or from about 60 micron to about 90 micron.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Example Hairstyling Formulations (Before Propellant)

| | A | B | C | D | E | F | G | H |
|---|---|---|---|---|---|---|---|---|
| Acrylates Copolymer [1] | 12.3% | 4.8% | 8.4% | — | — | — | — | — |
| Polyurethane-14/AMP-acrylates polymer blend [2] | — | 4.8% | 2.1% | 14.9% | 11% | — | — | — |
| Octylacrylamide/Acrylates/Butylaminoethyl/Methacrylate Copolymer [4] | — | — | 1.2% | — | 2.0% | — | — | — |
| Vinylpyrrolidone/Vinyl acetate Copolymer [5] | — | — | — | — | — | 10.8% | — | 9.58% |
| Methacrylic acid/hydroxyethylmethacrylate/various acrylate esters [3] | — | 2.40% | — | — | — | — | — | — |
| Polyquaternium-16 [6] | — | — | — | — | — | — | 6.7% | — |
| Chitosan [7] | — | — | — | — | — | — | 1.25% | — |
| Hydroxyethylcellulose dimethyldiallyammonium chloride [PQ4] [8] | — | — | — | — | — | — | — | 0.83% |
| 2-aminomethyl propanol (AMP) | 0.78% | 1.36% | 1.45% | — | — | — | — | — |
| Formic Acid | — | — | — | — | — | — | 0.40% | — |
| Fragrance | 0.03% | 0.10% | 0.10% | 0.10% | 0.10% | 0.18% | 0.15% | 0.2% |
| Dehyquart A-CA/Detex (cationic surfactant) | 0.4% | 0.4% | 0.4% | — | 0.40% | 0.4% | 0.4% | 0.4% |
| Dehydol LS 4 Deo N (Non-ionic surfactant) | 0.1% | 0.1% | — | 0.10% | — | — | — | 0.10% |
| PEG-12 dimethicone | 0.10% | — | — | — | — | — | — | — |
| Disodium EDTA | 0.13% | 0.13% | 0.13% | 0.13% | 0.13% | 0.13% | 0.13% | 0.13% |
| Phenoxyethanol | 0.50% | 0.50% | 0.50% | 0.50% | 0.50% | 0.50% | 0.50% | 0.50% |
| Methylparaben | 0.10% | 0.10% | 0.10% | 0.10% | 0.10% | 0.10% | 0.10% | 0.10% |
| Water | QSP | QSP | QSP | QSP | QSP | QSP | QSP | QSP |

KEY:
[1] = Balance CR;
[2] = DynamX H20;
[3] = Acudyne 1000;
[4] = Amphomer;
[5] = Luviskol VA64;
[6] = Luviquat FC550;
[7] = Hydagen ® HCMF;
[8] = Celquat L-200.

The percentages in the table are as a percent of the active polymer raw material in water. The final hairstyling polymer concentration in the hairspray product is diluted by the amount of propellant added to the can. The propellant may be in an amount of from about 35% to about 50%, by total weight of the hairstyling formulation and propellant. The propellant amount chosen for the example formulations above is 40% dimethyl ether (DME), by total weight of the hairstyling formulation and propellant.

Experimental

Table 2 depicts example alcohol-free hairspray products compared to two conventional alcohol-based hairspray products to illustrate the interconnected combination of the formulation polymer level, delivery rate, and formula viscosity limit aspects mentioned herein. Product examples 1 through 6 in the table below are based on the same hairstyling formulation, which is Example A of Table 1, and were prepared as 60% hairstyling formulation and 40% DME propellant. The amount of hairstyling polymer, however, differs.

TABLE 2

| Product | *Amount of hairstyling polymer (%) | Valve/ nozzle description | ‾ Delivery rate (g/sec) | Amount of hairstyling polymer per use # (g) | Amount of hairstyling formulation and propellant dispensed per use (g) | % water in total hairspray composition dispensed | Amount of water dispensed per use (g) | ‾ Average particle size distribution (Dv50) in micron | Kinematic viscosity of hairstyling formulation (cSt) |
|---|---|---|---|---|---|---|---|---|---|
| X | 3 | A | 0.8 | 0.186 | 6.2 | 3.10 | 0.19 | 54 | 15-30 |
| Y | 8 | B | 0.55 | 0.341 | 4.3 | 35.00 | 1.51 | 93 | 15-30 |
| 1 | 6 | C | 0.4 | 0.186 | 3.1 | 52.60 | 1.63 | 38 | 2.83 |
| 2 | 4.8 | D | 0.2 | 0.091 | 1.9 | 54.74 | 1.04 | 42 | 1.97 |
| 3 | 4.8 | N/A | 0.6 | 0.226 | 4.7 | 53.19 | 2.50 | N/A | 1.97 |
| 4 | 6 | E | 0.25 | 0.116 | 1.9 | 54.74 | 1.04 | 38 | 2.83 |
| 5 | 8-10 | D | 0.25 | 0.190 | 1.9 | 49.47 | 0.94 | N/A | 7-19 |
| 6 | 7.4 | F | 0.35 | 0.203 | 2.7 | 51.48 | 1.39 | 68 | 5.00 |

| Product | Enough polymer delivered for hold? | Acceptable drying time on hair? (Not too much water delivered) | Concentrate viscosity low enough to spray thorugh valve/ actuator package | Observations on performance |
|---|---|---|---|---|
| X | | | | Ethanol-based control |
| Y | | | | Ethanol-based control |
| 1 | YES | NO | YES | Unacceptable and sticky drying time from too much water dispensed. Minimal hold from low polymer amount needed for hold dispensed. |
| 2 | NO | YES | YES | Acceptable drying time from low level of water dispensed. Poor hold from not enough polymer dispensed. |
| 3 | YES | NO | YES | Very high level of water dispensed. Poor hold from immediate over-wetting of hairstyle with sticky/tacky feel and slow drying despite enough polymer dispensed. |
| 4 | LOW | YES | YES | Acceptable drying time from low level of water dispensed. Low hold from low level of polymer dispensed. |
| 5 | YES | YES | NO | Not able to dispense from high viscosity of hairspray formulation. Poor spraying (sputtering then clogged). |
| 6 | YES | YES | YES | Excellent drying time and hold from the right balance of enough polymer for hold and not too much water for acceptable dry time dispensed. |

KEY:

* = in the hairslyling formulation;

‾ = of the ejected composition;

# = one use is 7.75 sec in duration;

X = Wellaflex Level 3 Strong Hold hairspray (~45% ethanol);

Y = Herbal Essences Volumizing Max Hold hairspray (~25% ethanol);

A-F = see Table 3 below;

N/A = not applicable i.e. not measurable or paper example.

TABLE 3

Explanation of "Valve/nozzle description" in Table 2

| Valve/nozzle | Stem orifice, mm (inch) | Valve tail piece orifice, mm (inch) | Dip tube inner diameter, mm (inch) | Channel number and dimensions, mm (inch) | Insert orifice, mm (inch) |
|---|---|---|---|---|---|
| A | 0.32 (0.013) | 2.0 (0.078) | 3.1 (0.122) | None | 0.48 (0.019) |
| B | 0.41 (0.016) | 0.41 (0.016) | 3.1 (0.122) | 1 channel, 0.25 (0.010) | 0.50 (0.020) |
| C | 0.25 (0.010) | 1.27 (0.05) | 1.5 (0.059) | 1 channel, 0.33 (0.013) | 0.33 (0.013) |
| D | 0.33 (0.013) | 1.0 (0.039) | 1.0 (0.039) | 2 channels: 0.25 (0.010) x 0.33 (0.013) | 0.33 (0.013) + flow restrictor |
| E | 0.33 (0.013) | 1.0 (0.039) | 1.0 (0.039) | 2 channels: 0.25 (0.010) x 0.33 (0.013) | 0.33 (0.013) |
| F | 0.33 (0.013) | 1.0 (0.039) | 1.0 (0.039) | 2 channels: 0.25 (0.010) x 0.33 (0.013) | 0.50 (0.020) |

Analysis of Table 2:
  Products X and Y are ethanol-based control hairspray products.
  Product 1: uses valve/nozzle C, which comprises only 1 vapour tap, which is somewhat different from the "at least two vapour taps" claimed.
  Product 2: the hairstyling formulation comprises only 4.8% hairstyling polymer by total weight of the hairstyling formulation and propellant, which is somewhat different from the amount claimed.
  Product 3: the hairstyling formulation comprises only 4.8% hairstyling polymer by total weight of the hairstyling formulation and propellant, which is somewhat different from the amount claimed.
  Product 5: the hairstyling formulation (without propellant) has a kinematic viscosity of 7 to 19 cSt, which is somewhat different from the kinematic viscosity claimed.
Conclusions from Table 2:
  Of the spraying device features, hairstyling polymer level and hairstyling formulation kinematic viscosities evaluated, only the specific combination in product 6 meet all the criteria for a water-based hairspray that has excellent performance. Product 4 differs from product 6 in that the actuator insert orifice is larger for the latter versus the former. Product 4 provides low hold. Product 6 performs better because it delivers higher hair hold. Product 6 has a valve comprising two vapour taps. These are important for reducing the delivery rate, which is important for not overdosing the hair with wetness/water and is a special and new discovery since it is specific for research in the context of water-based hairsprays. The delivery rate must however be optimally balanced with the hairstyling polymer level in the hairstyling formulation in order to deliver enough polymer onto the hair for sufficient hairstyle hold performance. Furthermore, the kinematic viscosity of the hairstyling formulation is important in order for it to be sprayed through the orifices with sufficient mechanical break-up yet without clogging.
Analysis of Shernov (U.S. Pat. No. 5,304,368)
  The disclosure of reference Shernov is tested. In section F (column 4) of Shernov, it is stated that a valve having the following dimensions (lines 55-62) was used: stem orifice 0.011"; vapor tap: 0.016"; capilliary tubing ID: 0.040". Shernov states that each container was fitted with an actuator having a 0.018-inch exit orifice. It then goes on to state (lines 65-66 of column 4) that spray rate "was about 0.4 g/second" and the "particle size of the spray was about 50 microns". In the Example section in column 5 of Shernov, results of testing are shown in a table at the foot of this column.
  To test the accuracy of the disclosure of Shernov, four hairspray products are created using the spraying device and packaging information disclosed in Shernov: Can 1; Can 2; Can 3 and Can 4. Can 1 comprises 7.2% hairstyling polymer and 34% propellant (DME); Can 2 comprises 7.2% hairstyling polymer and 40% propellant (DME); Can 3 comprises 6.15% hairstyling polymer and 34% propellant (DME); Can 4 comprises 6.15% hairstyling polymer and 40% propellant (DME). The hairstyling polymer used is a water-soluble hairstyling polymer according to the present invention. All four cans (Can 1 to 4) are found to demonstrate unacceptable performance. In particular, the spray properties are found to vary greatly between the different cans and also vary dramatically as the hairspray formulation is gradually used up. Present FIG. 4 as attached herewith shows the relationship of pressure (axis Y, in psig [pounds per square inch]) versus percentage of can contents remaining (axis X, %). The percentage of the x axis is calculated by weight. Five different graphs are shown in present FIG. 4: graphs 1-4 and 5 (see legend). Graphs 1 to 4 relate to cans 1 to 4 (measured values) and can 5 is a graph created using the numbers in the Table at the foot of column 5 disclosed in Shernov. For example, in said Table in Shernov, it states that the product therein described should have a pressure of 61 psig when it is ¼ full i.e. 25% full. Indeed, the graph 5 shows a very flat graph and the pressure reduces minimally from 100% to 25% X. However, for Cans 1 to 4, the picture is somewhat different: the curves are not flat and show a dramatic pressure drop from 100% X to 50% X. In other words, the can pressure reduces significantly between a full can and a half full can. Unsurprisingly, the quality and features of the composition ejected from these cans varies wildly. It is not possible to state a specific delivery rate and/or average particle size distribution (Dv50) provided by any one of cans 1 to 4 because of the dramatic fluctuations as the hairstyling formulation is used up. Furthermore, significant problems with clogging and streaming are observed that made measurements of such properties difficult. In all cases, however, a delivery rate of below 0.2 g/sec (or no delivery rate due to clogging) is observed for all of cans 1 to 4 with about 50% X or less.

The values in the Table at the foot of column 5 disclosed in Shernov are not reproduced. Hence, it is concluded that the disclosure of Shernov is erroneous and its teaching would be discarded as irrelevant by the person having ordinary skill in the art.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An aerosol hairspray product wherein the product comprises:
    i. a pressurisable container (118) comprising a container wall (201) which encloses a reservoir (204) for storing a hairstyling formulation and a liquefied gas propellant;
    ii. the hairstyling formulation comprising:
        (a) from about 41% to about 60% water, by total weight of the hairstyling formulation and propellant; and
        (b) from about 5.0% to about 15% hairstyling polymer by total weight of the hairstyling formulation and propellant, wherein the hairstyling polymer is water-soluble; and
        (c) wherein the hairstyling formulation is free of alcohol;
    iii. a spraying device attached to the container (118) for dispensing the hairstyling formulation from the reservoir (204) of the container (118), wherein the spraying device comprises a valve (205) and a nozzle, wherein the valve comprises a valve body (113), a stem (107) and a spring means (108), wherein the valve body (113) houses an insert (109), wherein the insert comprises an insert orifice (109*a*) and at least two channels (110*a*, 110*b*), wherein the channels (110*a*, 110*b*) are tangentially disposed about the insert orifice (109*a*), wherein the valve body (113) comprises at least two vapour taps (211*a*, 211*b*), wherein the insert orifice (109*a*) is capable of being in liquid communication with the hairstyling formulation in the reservoir (204); wherein the channels (110*a*, 110*b*) converge on the insert orifice (109*a*): and wherein the insert orifice (109*a*) has a diameter of from about 0.020 inch (0.500 mm) to about 0.070 inch (1.778 mm); wherein the hairstyling formulation without propellant has a viscosity of from about 0.5 cSt to about 6 cSt, wherein the viscosity is measured at 20° C.+/−0.1 C; wherein the product comprises from about 40% to about 45% dimethylether, by total weight of the hairstyling formulation and propellant, wherein the spraying device is capable of causing the product to spray and wherein an ejected composition is sprayed, wherein the ejected composition consists of particles having an average particle size distribution (Dv50) of from about 40 microns to about 100 microns.

2. The product according to claim 1, from about 6% to about 12%, hairstyling polymer, by total weight of the hairstyling formulation and propellant.

3. The product according to claim 1, wherein the hairstyling formulation further comprises a surfactant.

4. The product according to claim 1, wherein the hairstyling formulation comprises a panthenol compound and/or a silicone compound.

5. The product according to claim 1, wherein the hairstyling polymer is an anionic polymer.

6. The product according to any claim 1, wherein the hairstyling polymer is a non-ionic polymer.

7. The product according to claim 1, wherein the hairstyling polymer is a cationic polymer.

8. The product according to claim 1, wherein the hairstyling polymer is an amphoteric polymer.

9. The product according to claim 5, wherein the hairstyling polymer is an anionic hairstyling polymer, and wherein the anionic hairstyling polymer is selected from: copolymers derived from acrylic acid such as the acrylic acid/ethylacrylate/N-tert-butylacrylamide terpolymers; Octylacrylamide/Acrylates/Butylaminoethyl/Methacrylate Copolymers; methacrylic acid/ester acrylate/ester methacrylates; Octylacrylamide/Acrylates/Butylaminoethyl Methacrylate Copolymer; methacrylic acid/hydroxyethylmethacrylate/various acrylate esters; acrylates/hydroxyethylmethacrylate; methacrylic acid/hydroxyethylmethacrylate/various acrylate esters; n-butyl methacrylate/methacrylic acid/ethyl acrylate copolymers; copolymers derived from crotonic acid, such as vinyl acetate/vinyl tertbutylbenzoate/crotonic acid terpolymers; and the crotonic acid/vinyl acetate/vinyl neododecanoate terpolymers; and mixtures thereof.

10. The product according to claim 1, wherein the hairstyling polymer is selected from the group consisting of: acrylates copolymers of two or more monomers of (meth) acrylic acid or one of their simple esters; octylacrylamide/acrylate/butylaminoethyl methacrylate copolymers; acrylates/hydroxyesters acrylates copolymers of butyl acrylate, methyl methacrylate, methacrylic acid, ethyl acrylate and hydroxyethyl methacrylate; polyurethane-14/AMP-acrylates copolymer blend; and mixtures thereof.

11. The product according to claim 1, wherein the insert orifice (109*a*) is capable of being in liquid communication with the hairstyling formulation in the reservoir (204) via a diptube (116) connected to a valve tailpiece (115).

12. The product according to claim 1, wherein the pressure inside the container is from about 3 bar to about 5 bar, at 20° C., or from 4 bar to 5 bar, at 20° C.

13. A method of styling hair comprising:
    a. providing the product according to claim 1;
    b. causing the product to spray and wherein an ejected composition is sprayed, wherein the ejected composition consists of particles having an average particle size distribution (Dv50) of from about 40 microns to about 100 microns.

14. The method of styling hair according to claim 13, wherein the particles have an average particle size distribution (Dv50) of from about 60 microns to about 90 microns.

\* \* \* \* \*